(12) United States Patent
Hughes et al.

(10) Patent No.: US 9,649,293 B2
(45) Date of Patent: May 16, 2017

(54) METHODS OF TREATING AN OVERWEIGHT SUBJECT

(71) Applicant: Zafgen, Inc., Boston, MA (US)

(72) Inventors: Thomas E. Hughes, Boston, MA (US); James E. Vath, Lynnfield, MA (US); Alan D. Cherrington, Nashville, TN (US)

(73) Assignees: Zafgen, Inc., Boston, MA (US); Vanderbilt University, Nashville, TN (US)

( * ) Notice: Subject to any disclaimer, the term of this patent is extended or adjusted under 35 U.S.C. 154(b) by 0 days.

(21) Appl. No.: 14/573,495

(22) Filed: Dec. 17, 2014

(65) Prior Publication Data

US 2015/0335608 A1 Nov. 26, 2015

Related U.S. Application Data

(63) Continuation of application No. 13/639,568, filed as application No. PCT/US2011/031608 on Apr. 7, 2011, now abandoned.

(60) Provisional application No. 61/321,600, filed on Apr. 7, 2010.

(51) Int. Cl.
| | | |
|---|---|---|
| A01N 43/647 | (2006.01) | |
| A61K 31/336 | (2006.01) | |
| C12N 15/113 | (2010.01) | |
| A61K 45/06 | (2006.01) | |
| A61K 31/196 | (2006.01) | |
| A61K 31/4025 | (2006.01) | |
| A61K 31/439 | (2006.01) | |

(52) U.S. Cl.
CPC .......... *A61K 31/336* (2013.01); *A61K 31/196* (2013.01); *A61K 31/4025* (2013.01); *A61K 31/439* (2013.01); *A61K 45/06* (2013.01); *C12N 15/1137* (2013.01); *C12Y 304/11018* (2013.01); *C12N 2310/11* (2013.01); *C12N 2310/14* (2013.01); *C12N 2310/531* (2013.01)

(58) Field of Classification Search
CPC .............................. A61K 31/336; C07K 16/40
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,198,406 A | 3/1993 | Mack et al. | |
| 5,204,345 A | 4/1993 | Kishimoto et al. | |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A | 6/1998 | Oku et al. | |
| 5,846,562 A | 12/1998 | Yanai et al. | |
| 5,900,431 A | 5/1999 | Molina et al. | |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,242,494 B1 | 6/2001 | Craig et al. | |
| 6,277,391 B1 | 8/2001 | Seo et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 | 12/2003 | Furuse et al. | |
| 6,803,382 B2 | 10/2004 | Tarnus et al. | |
| 6,877,863 B2 | 4/2005 | Wood et al. | |
| 6,898,392 B2 | 5/2005 | Karakama et al. | |
| 7,030,262 B2 | 4/2006 | BaMaung et al. | |
| 7,037,890 B2 | 5/2006 | Olson et al. | |
| 7,084,108 B2 | 8/2006 | Olson et al. | |
| 7,268,111 B2 | 9/2007 | Olson et al. | |
| 7,304,082 B2 | 12/2007 | Marino, Jr. et al. | |
| 7,718,695 B2 | 5/2010 | Kim et al. | |
| 8,367,721 B2 * | 2/2013 | Hughes ................ | A61K 31/336 514/475 |
| 8,642,650 B2 | 2/2014 | Hughes et al. | |
| 8,980,946 B2 | 3/2015 | Hughes | |
| 9,000,035 B2 | 4/2015 | Hughes | |
| 9,173,865 B2 | 11/2015 | Hughes | |
| 2002/0002152 A1 | 1/2002 | Craig et al. | |
| 2003/0220371 A1 | 11/2003 | Kallander et al. | |
| 2004/0067266 A1 | 4/2004 | Toppo | |

(Continued)

FOREIGN PATENT DOCUMENTS

| | | |
|---|---|---|
| EP | 068202 A1 | 1/1983 |
| WO | WO-98/56372 A1 | 12/1998 |

(Continued)

OTHER PUBLICATIONS

Kim et al., J.Mol.Endocrinol., Apr. 2007, vol. 38, pp. 455-465.*
Anderson, "The Use of Fumagillin in Aboebiasis," Anna NY Acad Sci. 30:5(6):1118-1124 (1952).
Benny et al., "An Orally Delivered Small-Molecule Formulation with Antiangiogenic and Anticancer Activity," Nat. Biotechnol. 26(7):799-807, doi/ 10.1038/nbt1415.Epub Jun. 29, 2008.
Bernier et al. "Fumagillin class inhibitors of methionine aminopeptidase-2", Drugs of the Future 30(5): 497-500, 2005.
Brakenhielm et al., "Angiogenesis Inhibitor, TNP-470, Prevents Diet-Induced and Genetic Obesity in Mice," Circulation Research, 94:1579-1588 (2004) jhttp://circres.ahajournals.org (accessed on Feb. 8, 2007).
Braunwald et al., "Obesity" in Harrison's Principles of Internal Medicine, 15th Ed, McGraw Hill (New York) pp. 479-486 (2001).
Chun et al. "Novel inhibitors targeted to methionine aminopeptidase 2 (MetAP2) strongly inhibit the growth of cancers in xenografted nude model", Int. J. Cancer 114(1):124-30, 2005.

(Continued)

*Primary Examiner* — Gyan Chandra
(74) *Attorney, Agent, or Firm* — Goodwin Procter LLP

(57) ABSTRACT

The invention generally relates in part to methods of effecting weight loss and/or improving glucose tolerance in a patient in need thereof, comprising administering a MetAP2 inhibitor.

10 Claims, 15 Drawing Sheets

(56) References Cited

U.S. PATENT DOCUMENTS

| | | |
|---|---|---|
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0192914 A1 | 9/2004 | Kallander et al. |
| 2004/0204472 A1 | 10/2004 | Briggs et al. |
| 2005/0004116 A1 | 1/2005 | Kallander et al. |
| 2005/0037994 A1 | 2/2005 | Kim et al. |
| 2005/0113420 A1 | 5/2005 | Nan et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2012/0322867 A1* | 12/2012 | Hughes ............... A61K 31/336 514/475 |
| 2013/0316994 A1 | 11/2013 | Hughes |
| 2014/0011870 A1 | 1/2014 | Hughes |
| 2014/0045934 A1 | 2/2014 | Hughes |
| 2014/0045935 A1 | 2/2014 | Hughes |
| 2014/0051752 A1 | 2/2014 | Hughes |
| 2014/0336251 A1 | 11/2014 | Hughes et al. |
| 2015/0150840 A1 | 6/2015 | Vath |
| 2015/0209320 A1 | 7/2015 | Hughes et al. |
| 2015/0209321 A1 | 7/2015 | Hughes |
| 2016/0038453 A1 | 2/2016 | Hughes et al. |
| 2016/0243073 A1 | 8/2016 | Hughes |

FOREIGN PATENT DOCUMENTS

| | | |
|---|---|---|
| WO | WO-99/39702 A2 | 8/1999 |
| WO | WO-99/57097 A2 | 11/1999 |
| WO | WO-99/59986 A1 | 11/1999 |
| WO | WO-99/59987 A1 | 11/1999 |
| WO | WO-00/64876 A1 | 11/2000 |
| WO | WO-02/26782 A2 | 4/2002 |
| WO | WO-02/42295 A2 | 5/2002 |
| WO | WO-02/083065 A2 | 10/2002 |
| WO | WO-03/027104 A1 | 4/2003 |
| WO | WO-2004/033419 A1 | 4/2004 |
| WO | WO-2005/066197 A2 | 7/2005 |
| WO | WO 2005/082349 * | 9/2005 |
| WO | WO-2005/082349 A1 | 9/2005 |
| WO | WO-2006/010498 A2 | 2/2006 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 A1 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 A2 | 4/2013 |
| WO | WO-2013/109735 A1 | 7/2013 |
| WO | WO-2013/109739 A1 | 7/2013 |
| WO | WO-2013/169727 A1 | 11/2013 |
| WO | WO-2013/169857 A1 | 11/2013 |
| WO | WO-2013/169860 A1 | 11/2013 |

OTHER PUBLICATIONS

Dider et al., "Antimicrosporidial Activities of Fumagillin, TNP-470, Ovalicin, and Ovalicin.Derivatives and Ovalicin Derivatives In Vitro and In Vivo," Antimicrobial Agents in Chemotherapy, 2146-2155 (2006).

DiPaolo et al., "Studies on the Carcinolytic Activity of Fumagillin and Some of its Derivatives," Antibio. Annu.6:541-546 (1958-1959).

Drevs et al., "Antiangiogenic Potency of FK866/K22, 175 a New Inhibitor of Intracellular NAD Biosynthesis, in Murine Renal Cell Carcinoma," Anticancer Res. 23(6C):4853-4858 (Nov.-Dec. 2003).

Dumas et al., "Synthesis and Structure Activity Relationships of Novel Small Molecule Cathepsin D Inhibitors," Bioorg Med Chem Lett., 9(17):2531-2536 (Sep. 6, 1999).

Eder et al., "Phase 1 Dose Escalation Safety & Tolerance Study of PPI-2458 in Subjects with Non-Hodgkin's Lymphoma or Solid Tumors", (Presented on Nov. 7-10, 2006 at EORTC-NCI-AACR Symposium on "Molecular Targets and Cancer Therapeutics.").

European Search Report for EP 09798793 dated Oct. 11, 2011, 9 pages.

Evdokimov et al., "Serendipitous discovery of novel bacterial methionine aminopeptidase inhibitors", Proteins. Feb. 15, 2007;66(3):538-46.

Everhart, "Contributions of Obesity and Weight Loss to Gallstone Disease", Ann Intern Med.,119(10):1029-1035, Nov. 13, 1993.

Garrabrant et al., "Small molecule inhibitors of methionine aminopeptidase type 2 (MetAP-2) fail to inhibit endothelial cell proliferation or formation of microvessels from rat aortic rings in vitro", Angiogenesis (2):91-96 (2004).

Garrison et al., "A metabolic basis for fibromyalgia and its related disorders: the possible role of resistance to thyroid hormone" Med Hypotheses. 61(2):182-189, Aug. 2000.

Han et al., "Design and Synthesis of Highly Potent Fumagillin Analogues from Homology Modeling for a Human MetAP-2," Bioorg Med Chem Lett.10(1):39-43, Jan. 3, 2000.

Huang et al., "Inhibition of monometalated methionine aminopeptidase: inhibitor discovery and crystallographic analysis", J Med Chem. Nov. 15, 2007;50(23):5735-42. Epub Oct. 19, 2007.

Ingber et al., "Synthetic analogues of fumagillin that inhibit angiogenesis and suppress tumour growth," Nature 348(6301):555-557, Dec. 6, 1990.

International Search Report and Written Opinion for Internatonal Application No. PCT/US2011/031608, mailed Aug. 19, 2014, 16 pages.

International Search Report completed on Mar. 2, 2011, for International Application PCT/US2010/052050.

International Search Report for International Application No. PCT/US2011/020515, International Filing Date Jul. 1, 2011, 4 pages.

International Search Report for International Application No. PCT/US2011/020866, mailed Jul. 22, 2011, 8 pages.

International Search Report for International Application No. PCT/US2011/060127, mailed Jan. 2, 2012, 2 pages.

International Search Report for International Application No. PCT/US2011/062320, mailed Feb. 17, 2012, 3 pages.

International Search Report for International Application No. PCT/US2011/38352, International Filing Date May 27, 2011, 3 pages.

International Search Report for International Application No. PCT/US2012/000461, mailed May 2, 2013, 7 pages.

International Search Report for PCT/US2011/062421, mailed Feb. 17, 2012, 3 pages.

(56) References Cited

OTHER PUBLICATIONS

Jeong et al., "Total Synthesis and Antiangiogenic Activity of Cyclopentane Analogues of Fumagillol", Bioorg Med Chem Lett. Aug. 1, 2005;15(15):3580-3583.
Kawai et al., "Development of sulfonamide compounds as potent methionine aminopeptidase type II inhibitors with antiproliferative properties", Bioorg Med Chem Lett. Jul. 1, 2006;16(13):3574-7. Epub May 2, 2006.
Kim et al. "Depletion of methionine aminopeptidase 2 does not alter cell response to fumagillin or bengamides", Cancer Res. May 1, 2004;64(9):2984-7.
Kim et al., "Assessment of the Anti-Obesity Effects of the TNP-470 Analog, CKD-732", J Mol Endocrinol. Apr. 2007;38(4):455-65.
Kim et al., "Development of parenteral formulation for a novel angiogenesis inhibitor, CKD-732 through complexation with hydroxypropyl-beta-cyclodextrin," Int J Pharm. Mar. 19, 2004;272(12):79-89.
Kim et al., "General pharmacology of CKD-732, a new anticancer agent: effects on central nervous, cardiovascular, and respiratory system," Biol Pharm Bull. Feb. 2005;28(2):217-23.
Kruger, "TNP-470: An Angiogenesis Inhibitor in Clinical Development for Cancer", Expert Opin Investig Drugs. Jun. 2000;9(6):1383-96.
Lee et al., "Absorption, distribution, metabolism, and excretion of CKD-732, a novel antiangiogenic fumagillin derivative, in rats, mice, and dogs", Arch Pharm Res., 27(2):265-272 (2004).
Lijnen, et al. "Fumagillin Reduces Adipose Tissue Formation in Murine Models of Nutritionally Induced Obesity", Obesity (Silver Spring). Dec. 2010;18(12):2241-6. doi: 10.1038/oby.2009.503. Epub Jan. 21, 2010.
Luo et al "Discovery and Structural Modification of Inhibitors of Methionine Aminopeptidases from *Escherichia coli* and *Saccharomyces cerevisiae*", J Med Chem. Jun. 19, 2003;46(13):2631-40.
Ma et al. "Structural analysis of inhibition of *E. coli* methionine aminopeptidase: implication of loop adaptability in selective inhibition of bacterial enzymes", BMC Struct Biol. Dec. 19, 2007;7:84.
Masiero et al. "New Anti-angiogenesis Agents: Review of the Clinical Experience with Carboxyamido-Triazole (CAI), Thalidomide, TNP-470 and Interleukin-12", Angiogenesis. 1997;1(1):23-35.
McCowan et al. "Fumagillin (H-3), a New Antibiotic with Amebicidal Properties", Science. Feb. 23, 1951;113(2930):202-3.
Milkowski et al., Antiangiogenic Agents in Cancer Therapy, Chapter 22 "TNP-470," pp. 385-398, 2012.
Molina et al., "Potential Efficacy of Fumagillin in Intestinal Microsporidiosis Due to Enterocytozoon Bieneusi in Patients with HIV Infection: Results of a Drug Screening Study", AIDS. Nov. 1997;11(13):1603-1610.
Molina et al.,"Fumagillin Treatment of Intestinal Microsporidiosis", N Engl J Med., 346(25):1963-1969 (2002).
Molina et al.,"Trial of Oral Fumagillin for the Treatment of Intestinal Microsporidiosis in Patients with HIV Infection," AIDS. Jul. 7, 2000;14(10):1341-1348.
Mosteller "Simplified calculation of body-surface area" N Engl J Med. Oct. 22, 1987;317(17):1098.
Myung et al. "The identification of in vitro metabolites of CKD-732 by liquid chromatography/tandem mass spectrometry", Rapid Commun Mass Spectrom. 2002;16(21):2048-53.
Naganuma et al., "Metronomic Doxifluridine Chemotherapy Combined with the Anti-Angiogenic Agent TNP=470 Inhibits the Growth of Human Uterine Carcinosarcoma Xenografts", Cancer Sci. Aug. 2011;102(8):1545-52.
National Task Force on the Prevention and Treatment of Obesity (1993) "Very Low-Calorie Diets", JAMA 270(8):967-974.
Noel et al.,"Increased Risk of Acute Pancreatitis and Biliary Disease Observed in Patients with Type 2 Diabetes", Diabetes Care. May 2009;32(5):834-8. doi: 10.2337/dc08-1755. Epub Feb. 10, 2009.
Pagliarulo et al. "Gallstone disease and related risk factors in a large cohort of diabetic patients", Dig Liver Dis. Feb. 2004;36(2):130-4.
Picoul et al.,"Progress in fumagillin synthesis," Pure Appl. Chem., vol. 75, No. 2-3, pp. 235-249 (2003).
Rhee et al., "Angiogenesis inhibitor attenuates parathyroid hormone-induced anabolic effect," Biomed. Pharmacother., 63(1):63-68 (2009).
Rupnick, "Adipose Tissue Mass Can be Regulated Through the Vasculature," Proc. Natl. Acad.Sci USA., 99(16):10730-10735 (2002).
Seneca et al. "Amebiasis: a review. II. Laboratory diagnosis, differential diagnosis and therapy," Am J Dig Dis. Jul. 1956;1(7):310-22.
Sheppard et al. "3-Amino-2-hydroxyamides and related compounds as inhibitors of methionine aminopeptidase-2", Bioorg Med Chem Lett. Feb. 23, 2004;14(4):865-8.
Shin et al. "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy", Invest New Drugs. Apr. 2012;30(2):672-80.
Shin, "A Phase I Pharmacokinetic and Pharmacodynamic Stdy of CKD-732, an Antiangiogenic Agent, in Patients with Refractory Solid Cancer", Invest New Drugs 28:650-658, (2010) Published online Dec. 29, 2010.
Srikumar et al. "Structural insights on Brugia malayi transglutaminase with cinnamoyl derivatives—a molecular docking approach", International Journal of Pharma and Bio Sciences 3(3):998-1006, 2012.
Teicher et al., "Antiangiogenic Agents in Cancer Therapy" pp. 385-398, 1999.
Towbin et al., "Proteomics-based target identification: bengamides as a new class of methionine aminopeptidase inhibitors," J. Biol. Chem. Dec. 26, 2003;278(52):52964-52971.
Vedantham et al.,"Studies towards the synthesis of methionine aminopeptidase inhibitors: diversification utilizing a ROMP-derived coupling reagent," J Comb Chem.10(2):195-203 (2008).
Wang et al. "Lead optimization of methionine aminopeptidase-2 (MetAP2) inhibitors containing sulfonamides of 5,6-disubstituted anthranilic acids", Bioorg Med Chem Lett. May 15, 2007;17(10):2817-22. Epub Feb. 25, 2007.
Wang et al. "Tumor Suppression by a Rationally Designed Reversible Inhibitor of Methionine Aminopeptidase-2", Cancer Res. 63:7861-7869, 2003.
Wang et al.,"Discovery of inhibitors of *Escherichia coli* methionine aminopeptidase with the Fe(II)-form selectivity and antibacterial activity," J. Med. Chem. Oct. 9, 2008;51(19):6110-6120.
Weinsier et al.,"Gallstone Formation and Weight Loss," Obes Res. Jan. 1993;1(1):51-6.
Weinsier et al.,"Medically Safe Rate of Weight Loss for the Treatment of Obesity: A Guideline Based on Risk of Gallstone Formation," Am. J. Med. Feb. 1995;98(2):115-117.
Winter et al.,"Endothelial αvβ3 Integrin-Targeted Fumagillin Nanoparticles Inhibit Angiogenesis in Atherosclerosis," Arterioscler Thromb Vasc Biol. Sep. 2006;26(9):2103-2109.
Written Opinion for International Application No. PCT/US2009/066816, mailed Apr. 8, 2010, 3 pages.
Written Opinion for International Application No. PCT/US2011/060127, mailed May 10, 2013, 4 pages.
Written Opinion for International Application No. PCT/US2011/062320, mailed May 29, 2013, 5 pages.
Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res. May 1995;12(5):653-7.
Yanai, et al., "Antitumor Activity of a Medium-Chain Triglyceride Solution of the Angiogenesis Inhibitor TNP-470 (AGM-1470) when Administered Via the Hepatic Artery to Rats Bearing Walker 256 Carcinosarcoma in the Liver," J. Pharmacol Exp Ther. Dec. 1994;271(3):1267-73.
Zhang et al., "Angiogenesis inhibitors specific for methionine aminopeptidase 2 as drugs for malaria and leishmaniasis," J. Biomed. Sci. Jan.-Feb. 2002;9(1):34-40.

\* cited by examiner

Brown adipose tissue content:
DIO + 1 mg/kg fumagillin

Brown adipose tissue content:
diet-induced obesity (DIO)

METHODS OF TREATING AN OVERWEIGHT SUBJECT

CROSS REFERENCE TO RELATED APPLICATIONS

This application is a continuation of U.S. application Ser. No. 13/639,568, which has a 35 U.S.C. 371 (c) date of Feb 25, 2013 and is the U.S. national stage of International (PCT) Patent Application Serial No. PCT/US2011/031608, filed Apr 7, 2011, which claims the benefit of U.S. Ser. No. 61/321,600, filed Apr 7, 2010, each of which is incorporated by reference in its entirety.

BACKGROUND

Type 2 diabetes is a growing health problem affecting more than 20 million people. Type 2 diabetes is often associated with obesity or with weight gain, although patients with normal weight can also suffer from this disease. The pre-diabetic states of impaired glucose tolerance and/or impaired fasting glucose are common indicators of future development of this disease.

Impaired glucose tolerance is typically defined as two hour glucose levels of 140 to 199 mg/dL (7.8 to 11 mmol) on a 75 g oral glucose tolerance test. The criteria for impaired fasting glucose is typically either of: a fasting plasma glucose level form 6.1 mmol/l (110 mg/dL) to 6.9 mmol/l (125 mg/dL, or a fasting plasma glucose level from 5.6 mmol/L (100 mg/dL) to 6.9 mmol/L (125 mg/dL). Impairments of glucose tolerance persist and often worsen in individuals who progress to develop type 2 diabetes, such that elevated glucose levels in the fed condition are a hallmark of both impaired glucose tolerance and type 2 diabetes.

Treatment modalities typically include lifestyle management such as weight loss, limiting carbohydrate intakes, and regular exercise. Reducing excess weight, in e.g. an overweight patient, can be challenging, however, at least in part because most diet or pharmaceutical interventions result in a regain of most weight once discontinued. For example, most anti-obesity or weight loss medications fail to produce durable weight loss.

MetAP2 encodes a protein that functions at least in part by enzymatically removing the amino terminal methionine residue from certain newly translated proteins such as glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). However, such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Methods of treating overweight subjects that are more effective than e.g. dieting alone are clearly needed, as well as methods of treating patient suffering from diabetes or glucose intolerance.

SUMMARY

This disclosure generally relates to methods of effecting weight loss in a subject or patient that comprises administering a pharmaceutically effective amount of a MetAP2 inhibitor to a patient in need thereof, e.g., a human or a companion animal such as a cat or a dog.

In one embodiment, a method of effecting weight loss in a patient in need thereof is provided (e.g. an overweight or obese patient), comprising administering a pharmaceutically effective amount of a MetAP2 inhibitor to said patient. Such methods may result in, for example, durable weight loss maintained for at least about 1 month, 2 months, 6 months, 1 year, 5 years or more.

Contemplated MetAP2 inhibitors include substantially irreversible inhibitors, such as e.g., fumagillin, fumagillol or fumagillin ketone derivative, siRNA, shRNA, an antibody, or a antisense compound, or, e.g., O-(4-dimethylaminoethoxycinnamoyl)fumagillol and pharmaceutically acceptable salts thereof. In another embodiment, a contemplated MetAP2 inhibitor may be substantially reversible inhibitor.

A method of reducing weight of a patient in a patient in need thereof is contemplated herein that comprises administering a pharmaceutically effective amount of a MetAP2 inhibitor to said patient wherein the metabolic rate of the patient is not substantially reduced as compared to the metabolic rate of a diet only patient on an energy restricted diet alone. Also provided herein is a method of restoring normal metabolic action in an overweight or obese patient in need thereof, comprising administering a pharmaceutically effective amount of a MetAP2 inhibitor to said patient.

In an embodiment, a method of improving, increasing, and/or glucose tolerance in patient (e.g. an overweight, obese or diabetic patient), in need thereof is provided that comprises administering a pharmaceutically effective amount of a MetAP2 inhibitor to said patient. Such a patient may be suffering from type 2 diabetes.

MetAP2 inhibitors may be administered parenterally, non-parenterally, orally, buccally or sublingually, topically, rectally, or transdermally in at least some disclosed methods. In some disclosed methods, a MetAP2 inhibitor may be administered subcutaneously or intravenously. In some embodiments, administration of a MetAP2 inhibitor may occur at least daily, or every other day, or at least weekly.

Also contemplated herein is a method for reducing the amount or frequency of administering supplemental insulin in a patient suffering from type 2 diabetes, comprising a pharmaceutically effective amount of a MetAP2 inhibitor.

Disclosed methods may further comprise co-administering an additional weight loss agent and/or hypoglycemic agent, and/or may further comprise administering a calorie or joule restricted diet to a patient.

DETAILED DESCRIPTION

Overview

Figure 1:
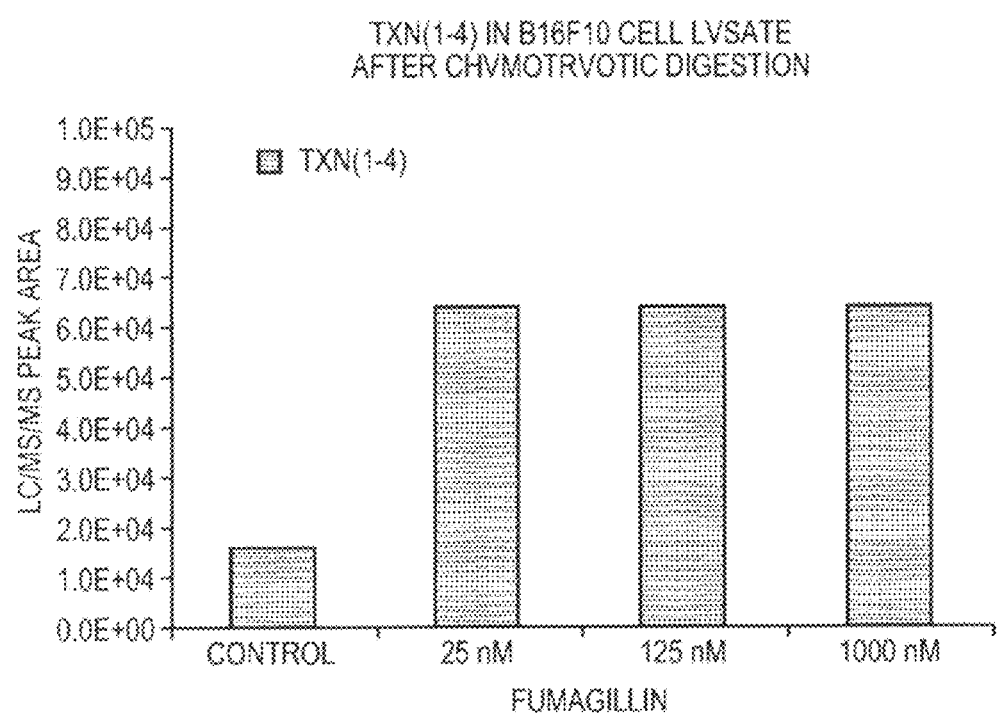
FIG. 1 is a bar graph showing TXN(104) in B16F10 cell lysate after chymotryptic digest.

Obesity and being overweight refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, degree of excess body fat, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using the formulas: SI units: BMI=weight(kg)/(height$^2$(m$^2$)), or US units: BMI=(weight(lb)*703)/(height$^2$(in$^2$)).

In accordance with the U.S. Centers for Disease Control and Prevention (CDC), an overweight adult has a BMI of 25 kg/m$^2$ to 29.9 kg/m$^2$, and an obese adult has a BMI of 30 kg/m, or greater. A BMI of 40 kg/m$^2$ or greater is indicative of morbid obesity or extreme obesity. For children, the definitions of overweight and obese take into account age and gender effects on body fat.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass may involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Another method is fan-beam dual energy X-ray absorptiometry (DEXA). DEXA allows body composition, particularly total body fat and/or regional fat mass, to be determined non-invasively.

Without being limited by any particular theory or mechanism of action, it is believed that fat oxidation and lipolysis are stimulated through treatment with inhibitors of MetAP2 that enhance the level and function of thioredoxin and/or over-rides the inhibitory effects of hyperinsulinemia related at least in part to insulin-stimulation and/or over-rides the inhibitory effects of high fat diet induced NADPH oxidase activity. A coordinated action can be induced which leads to a physiological reduction in body adiposity through increased loss of fat tissue-associated triglyceride, increased metabolism of free fatty acids by the liver with increased ketone body formation, and reduced food intake. These effects are evident at doses of a MetAP2 inhibitor that do not substantially modulate angiogenesis.

Figure 5A:
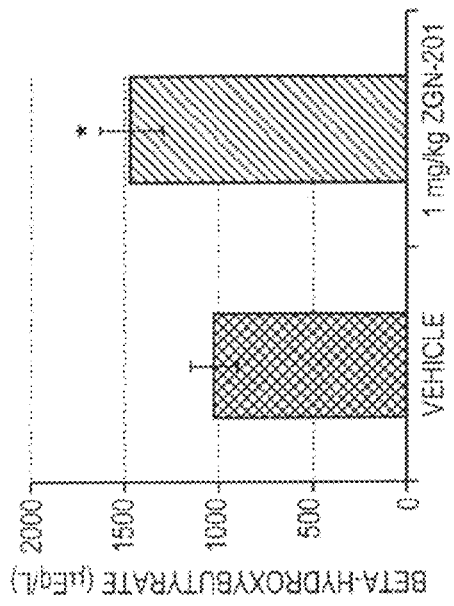
FIG. 5A is a bar graph showing the concentration of beta-hydroxybutyrate in mice fed a high fat diet (vehicle) or mice fed a high-fat diet plus oral administration of fumagillin for ten days at the concentrations indicated
Figure 5B:
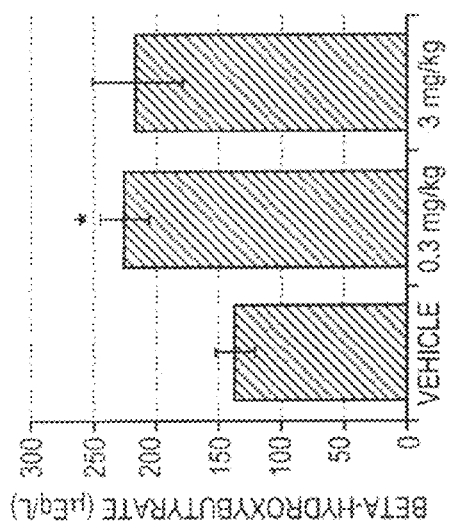
FIG. 5B is a bar graph showing the concentration of nonesterified fatty acid concentrations under the conditions described for FIG. 5A.

In obese and/or hyperinsulinemic patients, liver PKA function may be suppressed secondary to elevated NADPH oxidase expression. Ketone body production and utilization are typically suppressed in an obese patient, potentially reducing hepatic satiety signals and increasing food consumption. However, administration of a MetAP2 inhibitor, without being limited by an theory, leads to activation of adipose tissue lipase activity and/or stimulating production and/or activity of the rate-limiting enzyme of beta-hydroxybutyrate production (3-hydroxymethyl glutaryl CoA synthase), leading to elevated ketone body production, as illustrated in e.g. FIG. 5.

The coordinated and physiologic induction of anti-obesity activities mediated by the methods of the present invention may lead to a healthy reduction in tissue levels of triglyceride, diacylglycerol, and other fat-related mediators and oxidants, and can result in a new steady state situation that favors lean body composition and increased whole body energy metabolism. Without being bound by any theory, it is believed that the mechanistic cascade activated by MetAP2 inhibitors leads to fat tissue being converted to ketone bodies and burned as fuel, unlike existing therapies (including e.g., calorie or energy restricted diets) that target central control of food intake and that may carry adverse side effects (e.g. adverse neurological side effects). Partly as a consequence of improved metabolic function of the liver, glucose uptake by the liver is improved, reducing glucose concentrations in circulation and reducing the demand for insulin secretion and improving pancreatic beta cell function. Further, therapeutically effective doses contemplated herein will not typically induce any anti-angiogenic action.

Methods provided herein may substantially increase or stabilize glucose tolerance in a patient, for example, may increase glucose deposition as glycogen in a patient such as an overweight, obese, and/or diabetic patient or a patient that has reduced glucose tolerance.

MetAP2 Inhibitors

MetAP2 inhibitors refer to a class of molecules that inhibit the activity of MetAP2, e.g., the ability of MetAP2 to cleave the N-terminal methionine residue of newly synthesized proteins to produce the active form of the protein, or the ability of MetAP2 to regulate protein synthesis by protecting the subunit of eukaryotic initiation factor-2 (eIF2) from phosphorylation.

Exemplary MetAP2 inhibitors may include irreversible inhibitors that covalently bind to MetAP2. For example, such irreversible inhibitors include fumagillin, fumagillol, fumagillin ketone, Fumagillin refers to all stereoisomers, and can be represented by the following structure:

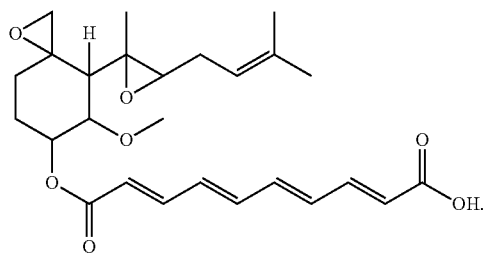 [SMILES: COC1C(OC(=O)/C=C/C=C/C=C/C=C/C(=O)O)CCC2(CO2)C1C1(C)OC1CC=C(C)C]

Fumagillol refers to all stereoisomers of the following structure:

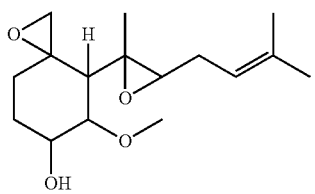

Fumagillin ketone refers to all stereoisomers of the following structure, and can be represented by the following structure:

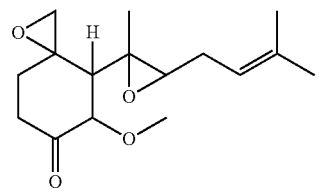

Derivatives and analogs of fumagillin, and pharmaceutically acceptable salts thereof are contemplated herein as irreversible MetAP2 inhibitors, such as O-(4-dimethylaminoethoxycinnamoyl)fumagillol (CKD-732, also referred to herein as Compound A), O-(3,4,5-tri methoxycinnamoyl)fumagillol, O-(4-chlorocinnamoyl)fumagillol; O-(4-aminocinnamoyl)fumagillol; O-(4-dimethylaminoethoxycinnamoyl)fumagillol; O-(4 methoxycinnamoyl)fumagillol; O-(4-dimethylaminocinnamoyl)fumagillol; O-(4 hydroxycinnamoyl)fumagillol; O-(3,4-dimethoxycinnamoyl)fumagillol; O-(3,4-methylenedioxycinnamoyl)fumagillol; O-(3,4,5-trimethoxycinnamoyl)fumagillol; O-(4-nitrocinnamoyl)fumagillol; O-(3,4-dimethoxy-6-aminocinnamoyl)fumagillol; O-(4-acetoxy-3,5-dimethoxycinnamoyl)fumagillol; O-(4-ethylaminocinnamoyl)fumagillol; O-(4-ethylaminoethoxycinnamoyl)fumagillol; O-(3-dimethylaminomethyl-4-methoxycinnamoyl)fumagillol; O-(4-trifluoromethylcinnamoyl)fumagillol; O-(3,4-dimethoxy-6-nitrocinnamoyl)fumagillol; O-(4-acetoxycinnamoyl)fumagillol; O-(4-cyanocinnamoyl)fumagillol; 4-(4-methoxycinnamoyl)oxy-2-(1,2-epoxy-1,5-dimethyl-4-hexenyl-3-methoxy-1-chloromethyl-1-cyclohexanol; O-(3,4,5-trimethoxycinnamoyl)fumagillol; O-(4-dimethylaminocinnamoyl)fumagillol; O-(3,4,5-trimethoxycinnamoyl)oxy-2-(1,2-epoxy-1,5-dimethyl-4-hexenyl)-3-methoxy-1-chloromethyl-1-cyclohexanol; O-(4-dimethylaminocinnamoyl)oxy-2-(1,2-epoxy-1,5-dimethyl-4-hexenyl)-3-me-thoxy-1-chloromethyl-1-cyclohexanol; O-(3,5-dimethoxy-4-hydroxycinnamoyl)fumagillol or O-(chloracetyl-carbamoyl)fumagillol (TNP-470).

Fumagillin, and some derivatives thereof, have a carboxylic acid moiety and can be administered in the form of the free acid. Alternatively, contemplated herein are pharmaceutically acceptable salts of fumagillin, fumagillol, and derivatives thereof. Pharmaceutically acceptable salts illustratively include those that can be made using the following bases: ammonia, L-arginine, benethamine, benzathene, betaine, bismuth, calcium hydroxide, choline, deanol, diethanolamine, diethylamine, 2-(diethylamino)ethanol, ethylenediamine, N-methylglucamine, hydrabamine, 1H-imidazole, lysine, magnesium hydroxide, 4-(2-hydroxyethyl)morpholine, piperazine, potassium hydroxide, 1-(2-hydroxyethyl)pyrrolidine, sodium hydroxide, triethanolamine, zinc hydroxide, diclycohexlamine, or any other electron pair donor (as described in Handbook of Pharmaceutical Salts, Stan & Wermuth, VHCA and Wiley, Uchsenfurt-Hohestadt Germany, 2002). Contemplated pharmaceutically acceptable salts may include hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

Esters of the present invention may be prepared by reacting fumagillin or fumagillol with the appropriate acid under standard esterification conditions described in the literature (Houben-Weyl 4th Ed. 1952, Methods of Organic Synthesis). Suitable fumagillin esters include ethyl methanoate, ethyl ethanoate, ethyl propanoate, propyl methanoate, propyl ethanoate, and methyl butanoate.

In another embodiment, contemplated irreversible inhibitors of MetAP2 may include a siRNA, shRNA, an antibody or an antisense compound of MetAP2.

Further examples of MetAP2 inhibitors, are provided in the following references, each of which is hereby incorporated by reference: Olson et al. (U.S. Pat. No. 7,084,108 and WO 2002/042295), Olson et al. (U.S. Pat. Nos. 6,548,477; 7,037,890; 7,084,108; 7,268,111; and WO 2002/042295), Olson et al. (WO 2005/066197), Hong et al. (U.S. Pat. No. 6,040,337), Hong et al. (U.S. Pat. No. 6,063,812 and WO 1999/059986). Lee et al. (WO 2006/080591), Kishimoto et al. (U.S. Pat. Nos. 5,166,172; 5,698,586; 5,164,410; and 5,180,738), Kishimoto et al. (U.S. Pat. No. 5,180,735), Kishimoto et al. (U.S. Pat. No. 5,288,722), Kishimoto et al. (U.S. Pat. No. 5,204,345). Kishimoto et al. (U.S. Pat. No. 5,422,363), Liu et al. (U.S. Pat. Nos. 6,207,704; 6,566,541; and WO 1998/056372). Craig et al. (WO 1999/057097), Craig et al. (U.S. Pat. No. 6,242,494), BaMaung et al. (U.S. Pat. No. 7,030,262), Comess et al. (WO 2004/033419), Comess et al. (US 2004/0157836). Comess et al. (US 2004/0167128), Henkin et al. (WO 2002/083065), Craig et at, (U.S. Pat. No. 6,887,863), Craig et al. (US 2002/0002152), Sheppard et al. (2004, Bioorganic & Medicinal Chemistry Letters 14:865-868), Wang et al. (2003, Cancer Research 63:7861-7869), Wang et al. (2007, Bioorganic & Medicinal Chemistry Letters 17:2817-2822). Kawai et al. (2006, Bioorganic & Medicinal Chemistry Letters 16:3574-3577), Henkin et al. (WO 2002/026782). Nan et al. (US 2005/0113420). Luo et al. (2003, J. Med. Chem., 46:2632-2640), Vedantham et al. (2008, J. Comb. Chem. 10:195-203). Wang et al. (2008, J. Med. Chem., XXXX, Vol. xxx. No. xx). Ma et al. (2007, BMC Structural Biology, 7:84) and Huang et al. (2007, J. Med. Chem., 50:5735-5742). Evdokimov et al. (2007, PROTEINS: Structure. Function, and Bioinformatics, 66:538-546), Garrabrant et al. (2004, Angiogenesis 7:91-96), Kim et al. (2004, Cancer Research, 64:2984-2987), Towbin et al. (2003. The Journal of Biological Chemistry, 278(52):52964-52971), Marino Jr. (U.S. Pat. No. 7,304,082). Kallender et al. (U.S. patent application number 2004/0192914), and Kallender et al. (U.S. patent application numbers 2003/0220371 and 2005/0004116). In some embodiments, contemplated MetAP2 inhibitors do not include fumagillin, fumagillol, fumagillin ketone, CKD-732/Compound A, and/or TNP-470.

For example, contemplated MetAP2 inhibitors may include:

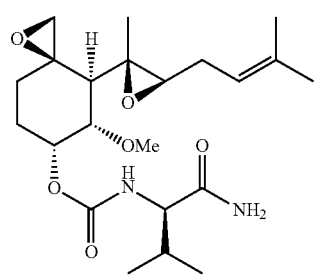
(B)

-continued

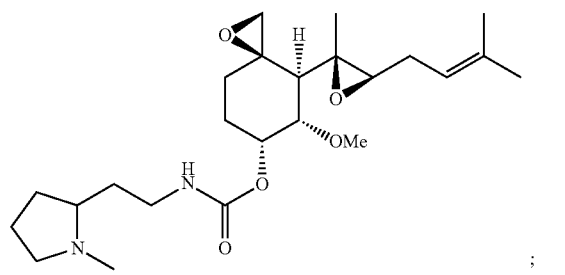
(C)

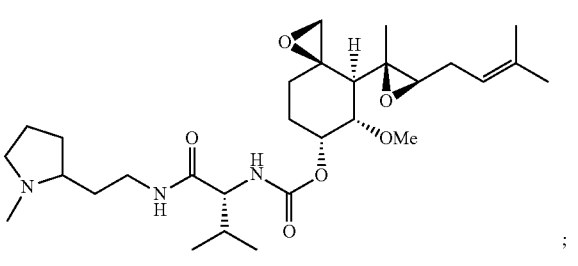
(D)

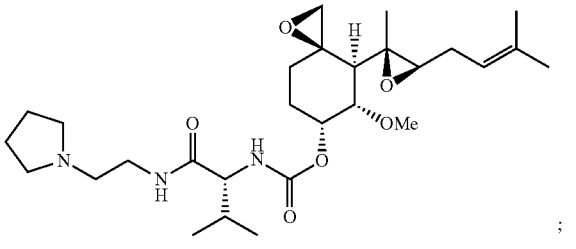
(E)

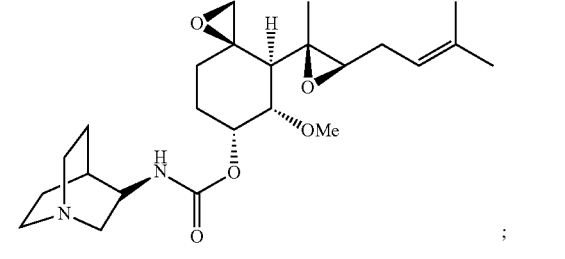
(F)

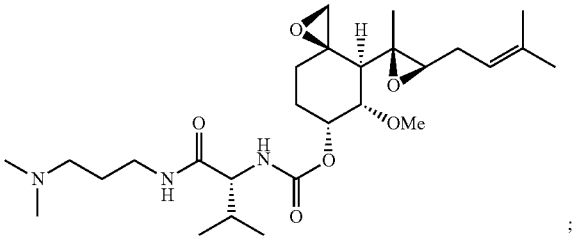
(G)

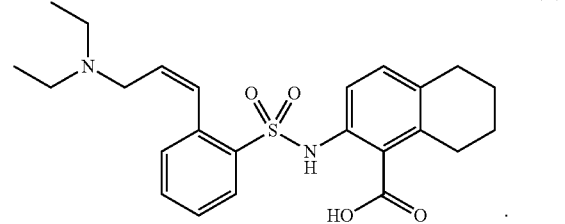
(H)

Methods

A method of treating obesity in a patient in need thereof is provided herein, comprising non-parenterally administering a pharmaceutically effective amount of a MetAP2 inhibitor to said patient. In some embodiments, a contemplated pharmaceutically effective amount of a MetAP2 as described below, does not substantially modulate or suppress angiogenesis, but is still effective as MetAP2 inhibitor. The term "angiogenesis" is known to persons skilled in the art, and refers to the process of new blood vessel formation, and is essential for the exponential growth of solid tumors and tumor metastasis. For example, provided herein is a method of treating obesity in a patient in need thereof, comprising administering a pharmaceutically effective amount of a MetAP2 inhibitor to said patient, wherein substantially no loss of new blood vessels in fat deposits or other tissue compartments occur as compared to a patient being treated for obesity using an energy restricted diet alone.

For example, fumagillin-class molecules irreversibly inhibit enzymatic activity of MetAP2, leading to N-terminal acetylation and stabilization of these proteins at doses considerably lower than those required to suppress angiogenesis or tumor growth in vivo. Without being limited to any theory, the long-lasting covalent inhibition of MetAP2 enzymatic activity driven by such MetAP2 inhibitors may be responsible for the segregation of angiogenic effects from metabolic responses mediated by increased thioredoxin and/or glyceraldehyde-3-phosphate levels in vivo. Alternatively, anti-tumor effects driven by angiogenesis inhibition may require a more thorough starvation of the tumor by heavily restricting blood supply, which requires high doses. Metabolic effects, however, may require a minor and incomplete perturbation of the system which occurs at lower doses and without any obvious direct effect on blood vessels. Metabolic effects that are largely dependent upon MetAP2 inhibition in the liver also may be elicited by treatment by e.g. administration of one or more MetAP2 inhibitors, such as those disclosed herein, that for example may effectively inactivate MetAP2 functions in the liver without providing sufficient exposure of the compounds to peripheral tissues to inhibit MetAP2.

Provided herein is a method of effecting weight loss in a patient in need thereof (e.g. an obese or overweight patient), comprising administering a pharmaceutically effective amount of a MetAP2 inhibitor to said patient, wherein, upon discontinuation of the MetAP2 inhibitor, the patient maintains a significant weight loss for a least about 1 month, 2 months 3 month, 6 months or a year or more. Such a patient may retain substantially more muscle mass as compared to body fat reduction in a patient using an energy restricted diet alone.

In some embodiments, disclosed methods, upon administration of said MetAP2 inhibitor e.g. daily or weekly, for about 3, 4, 5 or 6 months or more may result in at least a 5%, 10%, 20%, or 30%, or more weight loss based on the patient's original weight, which is maintained in the patient for e.g. 3 months, 6 months, 1 year, or even 5 years or more. In an embodiment, there may be a weight gain following treatment with therapeutically effective doses of MetAP2 inhibitors, but a patient durably maintains a lower body mass index as compared to a patient's body mass index before treatment.

In an embodiment, provided herein is a method of maintaining a specified weight in a formerly obese or overweight patient, comprising administering a pharmaceutically effective amount of a MetAP2 inhibitor to said patient. In another embodiment, provided herein is a method of inhibiting further weight gain in an overweight or obese patient, comprising administering a pharmaceutically effective amount of a MetAP2 inhibitor to said patient.

Also provided herein is a method for controlling or increasing glucose tolerance in a patient, such as an overweight, obese and/or diabetic patient, comprising administering a pharmaceutically effective amount of a MetAP2 inhibitor to said patient. Such methods may result in lowering a patient's glucose levels in a 75 g oral glucose tolerance 2 hour test to a normal range, e.g. about 70-140 mg/dL or about 5.5 mmmol/l or less. In another embodiment, disclosed methods may reduce levels of circulating glycated hemoglobin (HbA1c), a key and accepted biochemical indicator of long-term glycemic control.

For example, a method of restoring normal metabolic action in an obese or overweight patient in need thereof is provided, comprising administering a pharmaceutically effective amount of a MetAP2 inhibitor to said patient. In an embodiment, a method of reducing weight of a patient in a patient in need thereof is provided comprising administering a pharmaceutically effective amount of a MetAP2 inhibitor to said patient wherein the metabolic rate of the patient is not substantially reduced as compared to the metabolic rate of a diet only patient on an energy restricted diet alone.

Contemplated herein is a method of reducing the amount or frequency of administering supplemental insulin in a patient suffering from type 2 diabetes, comprising administering a pharmaceutically effective amount of a MetAP2 inhibitor to said patient. Such treatment may be directed to an obese or non-obese (e.g. an overweight patient (either diabetic or non-diabetic, including pre-diabetic), or a normal weight diabetic) patient.

In addition to being overweight or obese, a subject can further have an overweight- or obesity-related co-morbidities, i.e., diseases and other adverse health conditions associated with, exacerbated by, or precipitated by being overweight or obese. Because being overweight or obese is associated with other adverse health conditions or co-morbidities, for example diabetes, administering MetAP2 inhibitors brings a benefit in ameliorating, arresting development of or, in some cases, even eliminating, these overweight- or obesity-related conditions or co-morbidities. In some embodiments, methods provided herein may further include administering at least one other agent that is directed to treatment of these overweight- or obesity-related conditions.

Contemplated other agents include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazone); glucagon-like 1 peptide mimetics (e.g. exenatide and liraglutide); sodium-glucose cotransporter inhibitors (e.g., dapagliflozin), dipeptidylpeptidase 4 inhibitors such as vildagliptin, sitagliptin, saxagliptin, and alpha-glucosidase inhibitors (e.g., acarbose and meglitol), and/or those administered to treat cardiac disorders and conditions, such hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); rennin inhibitors (e.g., aliskiren), ACE inhibitors (benazepril hydrochloride, captopril enalapril maleate, fosinopril sodium, lisinopril, moexipril, quinapril hydrochloride, ramipril, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin, typically for treatment of dyslipidemia.

Other agents that may be co-administered (e.g. sequentially or simultaneously) include agents administered to treat ischemic heart disease including statins, nitrates (e.g., Isosorbide Dinitrate and Isosorbide Mononitrate), beta-blockers, and calcium channel antagonists, agents administered to treat cardiomyopathy including inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers, agents administered to treat cardiac infarction including ACE inhibitors, Angiotensin II receptor blockers, renin inhibitors, direct vasodilators, beta blockers, anti-arrhythmic agents and thrombolytic agents (e.g., Alteplase, Retaplase, Tenecteplase, Anistreplase, and Urokinase), agents administered to treat strokes including anti-platelet agents (e.g., Aspirin, Clopidogrel, Dipyridamole, and Ticlopidine), anticoagulant agents (e.g., Heparin), and thrombolytic agents, agents administered to treat venous thromboembolic disease including anti-platelet agents, anticoagulant agents, and thrombolytic agents, agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil, agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex, agents administered to treat sleep apnea include Modafinil and amphetamines, agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents, agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g., glucosamine and chondroitin sulfate), and artificial joint fluid, agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax), agents administered to treat polycystic ovary syndrome include insulin-sensitizers, combinations of synthetic estrogen and progesterone, Spironolactone, Eflornithine, and Clomiphene, agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone, agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Ulrofollitropin, Heparin, Follitropin alfa, and Follitropin beta, agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic, agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthene, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate), agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers, and other weight loss agents, including serotonin and noradrenergic re-uptake inhibitors-noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax.

In some embodiments, contemplated methods may further comprising assessing one or more indices of on-going weight loss, e.g. the ketone body production level in a patient; and optionally adjusting the amount administered; thereby optimizing the therapeutic efficacy of said MetAP2 inhibitor.

Administration and Formulation

Contemplated herein are formulations suitable for non-parenteral and parenteral administration of MetAP2 inhibitors.

Contemplated non-parenteral administration includes oral, buccal, transdermal (e.g. by a dermal patch), topical, inhalation, or sublingual administration, or e.g., ocular, pulmonary, nasal, rectal or vaginal administration. Parenteral administration includes subcutaneous and intravenous administration.

In another embodiment, provided herein are effective dosages, e.g. a daily dosage of a MetAP2 inhibitor, that may not substantially modulate or suppress angiogenesis. For example, provided here are methods that include administering doses of MetAP2 inhibitors that are effective for weight loss, but are significantly smaller doses than that necessary to modulate and/or suppress angiogenesis (which may typically require about 12.5 mg/kg to about 50 mg/kg or more). For example, contemplated dosage of a MetAP2 inhibitor in the methods described herein may include administering about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, or about 0.01 mg/day.

For example, an effective amount of the drug for weight loss in a patient may be about 0.0001 mg/kg to about 25 mg/kg of body weight per day. For example, a contemplated dosage may from about 0.001 to 10 mg/kg of body weight per day, about 0.001 mg/kg to 1 mg/kg of body weight per day, about 0.001 mg/kg to 0.1 mg/kg of body weight per day or about 0.005 to about 0.04 mg/kg or about 0.005 to about 0.049 mg/kg of body weight a day. In an embodiment a MetAP2 inhibitor such as disclosed herein (e.g. O-(4-dimethlyaminoethoxycinnamoyl)fumagillol), may be administered about 0.005 to about 0.04 mg/kg of a patient.

For example, provided herein is a method for treating obesity in a patient in need thereof, comprising administering, parenterally (e.g. intravenously) or non-parenterally, about 0.005 to about 0.04 mg/kg of a MetAP2 inhibitor selected from O-(4-dimethylaminoethoxycinnamoyl)fumagillol and pharmaceutically acceptable salts thereof (for example, an oxalate salt), to said patient. Such a method, upon administration of said MetAP2 inhibitor e.g. daily or weekly, for about 3, 4, 5 or 6 months or more may result in at least a 10%, 20%, 30%, or 40% or more weight loss based on the patient's original weight.

Contemplated methods may include administration of a composition comprising a MetAP2 inhibitor, for example, hourly, twice hourly, every three to four hours, daily, twice daily, 1, 2, 3 or 4 times a week, every three to four days, every week, or once every two weeks depending on half-life and clearance rate of the particular composition or inhibitor.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. For example, when about loss of about 20% body weight, about 30% body weight or more has been achieved. A treatment regimen can include a corrective phase, during which a MetAP2 inhibitor dose sufficient to provide reduction of excess adiposity is administered, followed by a maintenance phase, during which a lower MetAP2 inhibitor dose sufficient to prevent re-development of excess adiposity is administered.

For pulmonary (e.g., intrabronchial) administration, MetAP2 inhibitors can be formulated with conventional excipients to prepare an inhalable composition in the form of a fine powder or atomizable liquid. For ocular administration. MetAP2 inhibitors can be formulated with conventional excipients, for example, in the form of eye drops or an ocular implant. Among excipients useful in eye drops are viscosifying or gelling agents, to minimize loss by lacrimation through improved retention in the eye.

Liquid dosage forms for oral or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition may include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

When administered in lower doses, injectable preparations are also contemplated herein, for example, sterile injectable aqueous or oleaginous suspensions may be formulated according to the known art using suitable dispersing or wetting agents and suspending agents.

Compositions for rectal or vaginal administration may be suppositories which can be prepared by mixing a MetAP2 inhibitor with suitable non-irritating excipients or carriers such as cocoa butter, polyethylene glycol or a suppository wax which are solid at ambient temperature but liquid at body temperature and therefore melt in the rectum or vaginal cavity and release the active agent(s). Alternatively, contemplated formulations can be administered by release from a lumen of an endoscope after the endoscope has been inserted into a rectum of a subject.

Oral dosage forms, such as capsules, tablets, pills, powders, and granules, may be prepared using any suitable process known to the art. For example, a MetAP2 inhibitor may be mixed with enteric materials and compressed into tablets.

Alternatively, formulations of the invention are incorporated into chewable tablets, crushable tablets, tablets that dissolve rapidly within the mouth, or mouth wash.

EXAMPLES

The examples which follow are intended in no way to limit the scope of this invention but are provided to illustrate aspects of the disclosed methods. Many other embodiments of this invention will be apparent to one skilled in the art.

Example 1

Fumagillin Increases Levels of Thioredoxin-1 (TXN) in a Dose-dependent Manner

Figure 2:
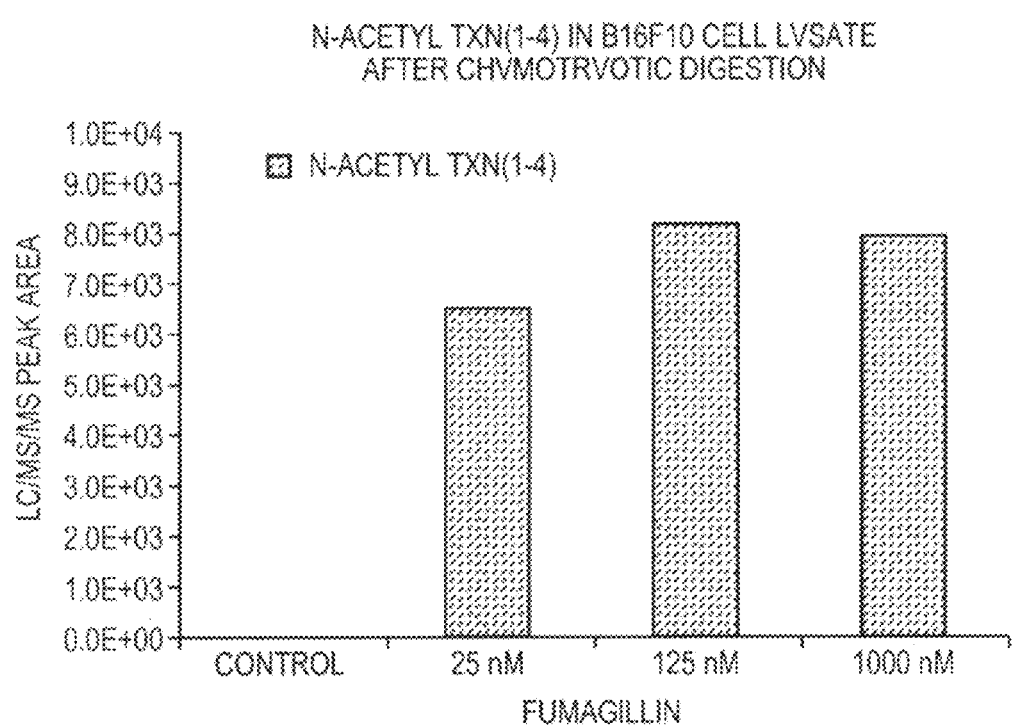
FIG. 2 is a bar graph showing N-acetyl TXN(1-4) in B16F10 cell lysate after chymotriptic digest.

B16F10 cells were treated with increasing concentrations of fumagillin. N-terminal chymotryptic fragments of TXN were measured by liquid chromatography/mass spectrometry (LC/MS). Fumagillin significantly increased the cellular level of TXN containing an intact N-terminal methionine [TXN(1-4)] and caused significant accumulation of N-acetyl TXN(1-4), consistent with a role for fumagillin as a MetAP2 inhibitor. See FIGS. 1-2. The EC50 of fumagillin to increase Met-TXN acetylated Met-TXN levels is <10 nM.

Figure 3:
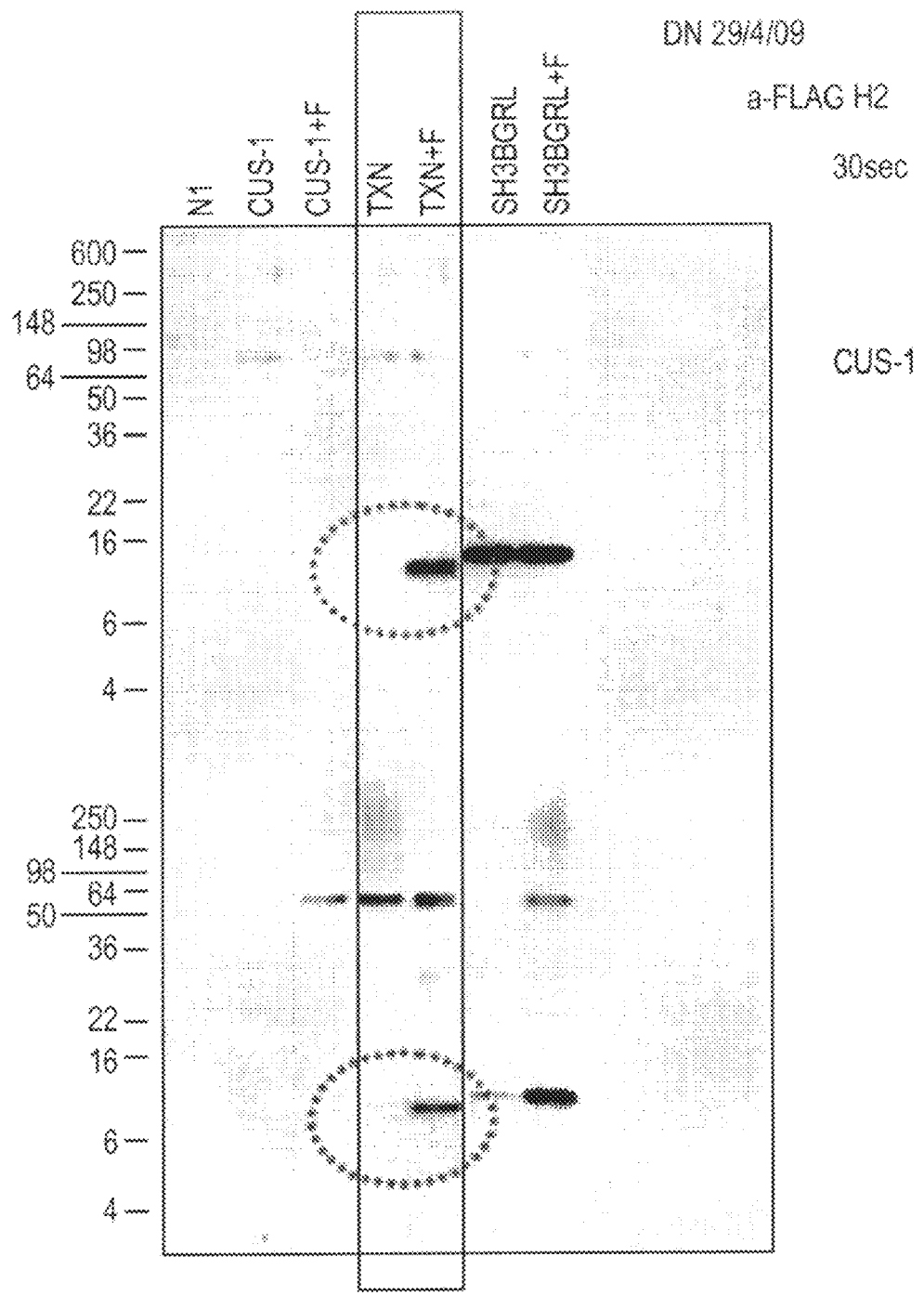
FIG. 3 is a photograph of a gel showing that fumagillin significantly increased TXN in both Cos-1 and 293T cells.
Figure 4:
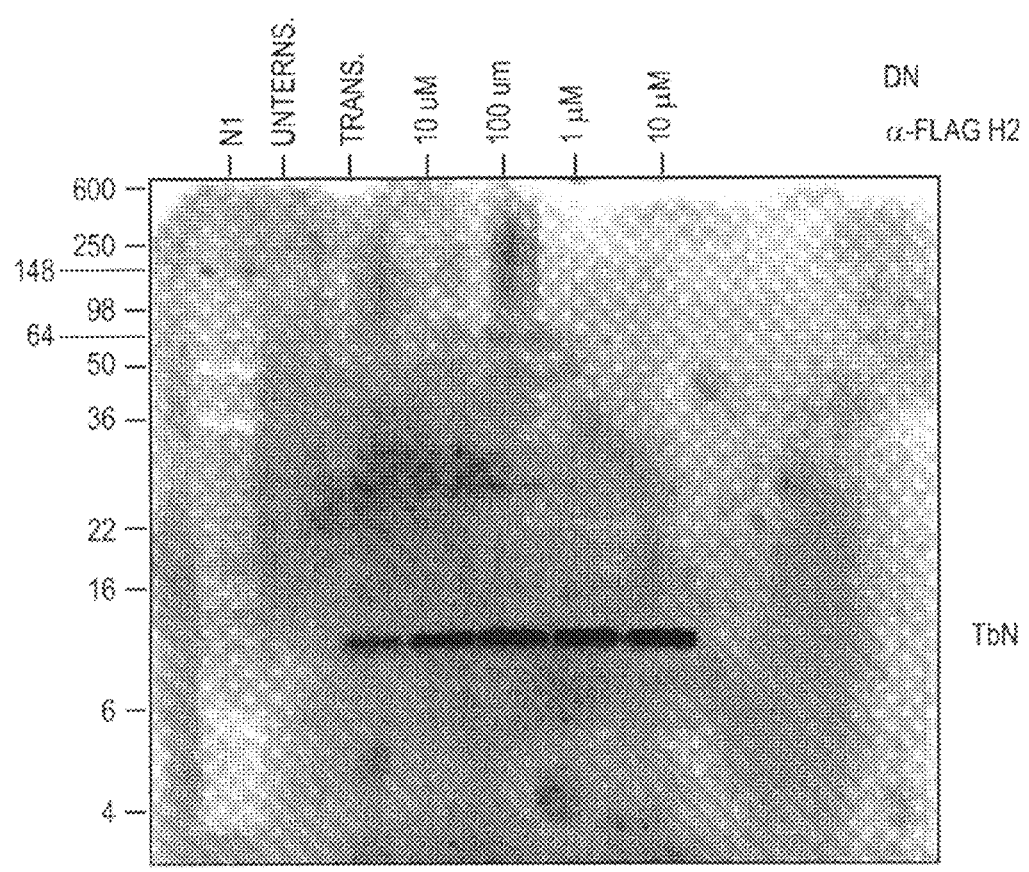
FIG. 4 is a photograph of a gel showing that EC50 of fumagillin to increase TXN levels is <10 nM.

Similar results were seen in Cos-1 and 293T cells that were transfected with FLAG-tagged TXN in the absence (TXN) and presence (TXN+F) of fumagillin. Fumagillin significantly increased the expression on TXN in both Cos-1 and 293T cells. See FIG. 3. EC50 of fumagillin to increase TXN levels is <10 nM. See FIG. 4.

Example 2

Oral Administration of Fumagillin Reduces Body Fat in Mammals

Figure 5C:
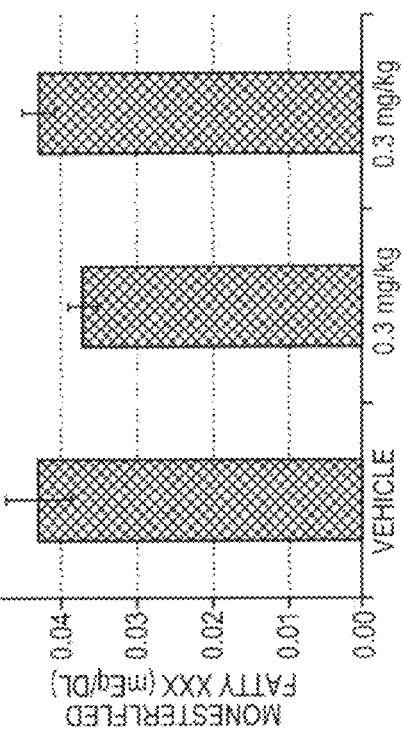
FIG. 5C is a bar graph showing the concentration of beta-hydroxybutyrate in mice fed a high fat diet (vehicle) or mice fed a high-fat diet plus oral administration of fumagillin for 250 days at the concentrations indicated.

Oral administration of the MetAP2 inhibitor fumagillin causes an increase in circulating ketone bodies, as measured by concentration of beta hydroxybutyrate, which indicates an increase in the breakdown of stored fat. C57BL/6 mice conditioned on a high fat diet (also referred to as a diet-induced obese diet or DIO) were treated with fumagillin (ZGN-201) administered by oral gavage at doses of 0.3 or 3 mg/kg daily for 10 days resulting in an increase in beta hydroxybutyrate (FIG. 5A) concentrations, without an increase in free fatty acid concentration (FIG. 5B) as well as a reduction in body weight by 7 to 15 percent (data not shown). Increased hydroxybutyrate concentration persisted at longer time points, as was seen in C57BL/6 mice conditioned on a high fat diet and treated with fumagillin (ZGN-201) as a diet admixture at a dose of 1 mg/kg daily for 250 days (FIG. 5C).

Figure 6:
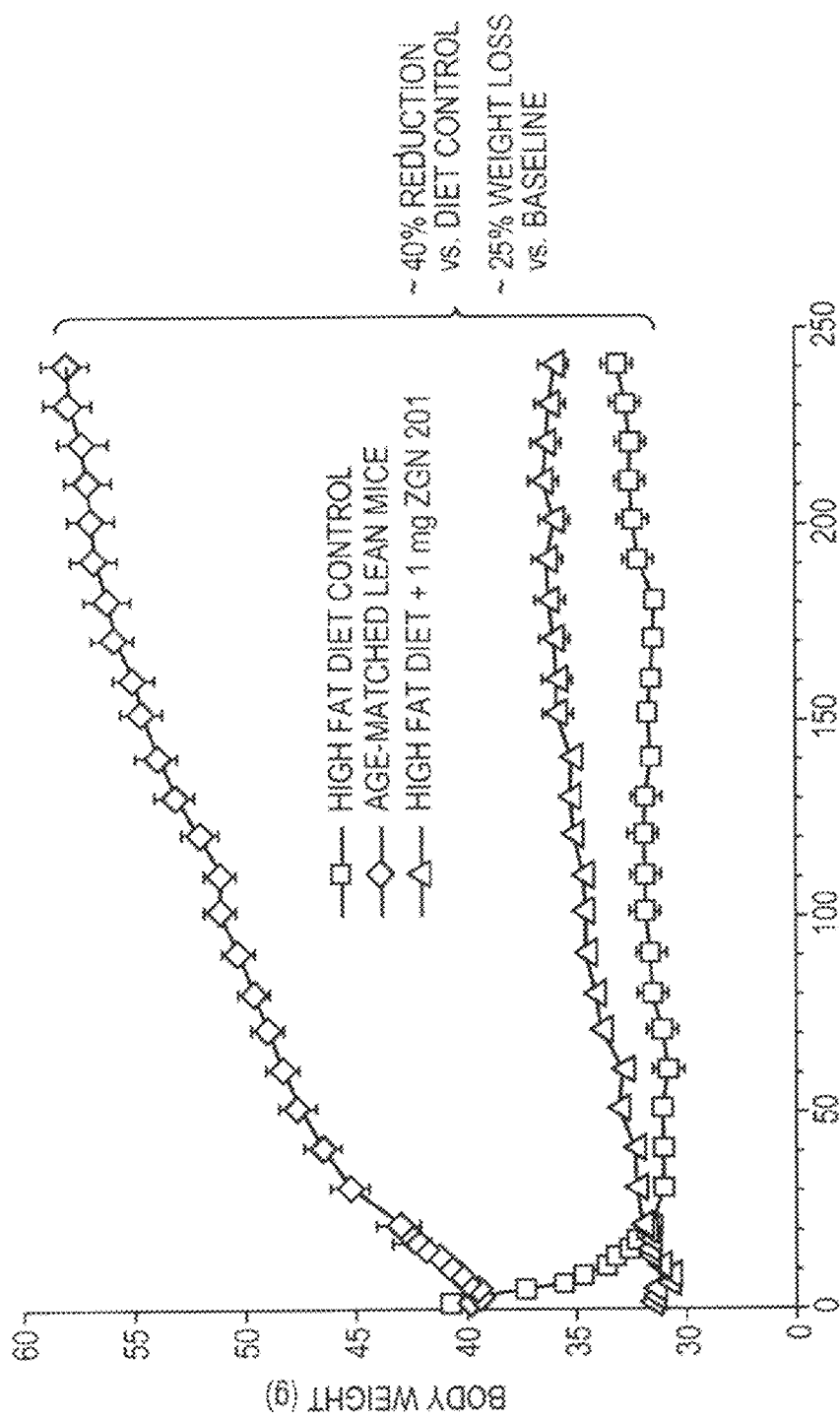
FIG. 6 is a line graph showing the body weight over time of high-fat diet-fed C57BL/6 mice treated with 1 mg/kg fumagillin (squares) or vehicle (diamonds) for 250 days. Age-matched lean C57BL/6 mice maintained on normal mouse chow diet are shown for comparison (triangles).
Figure 7:
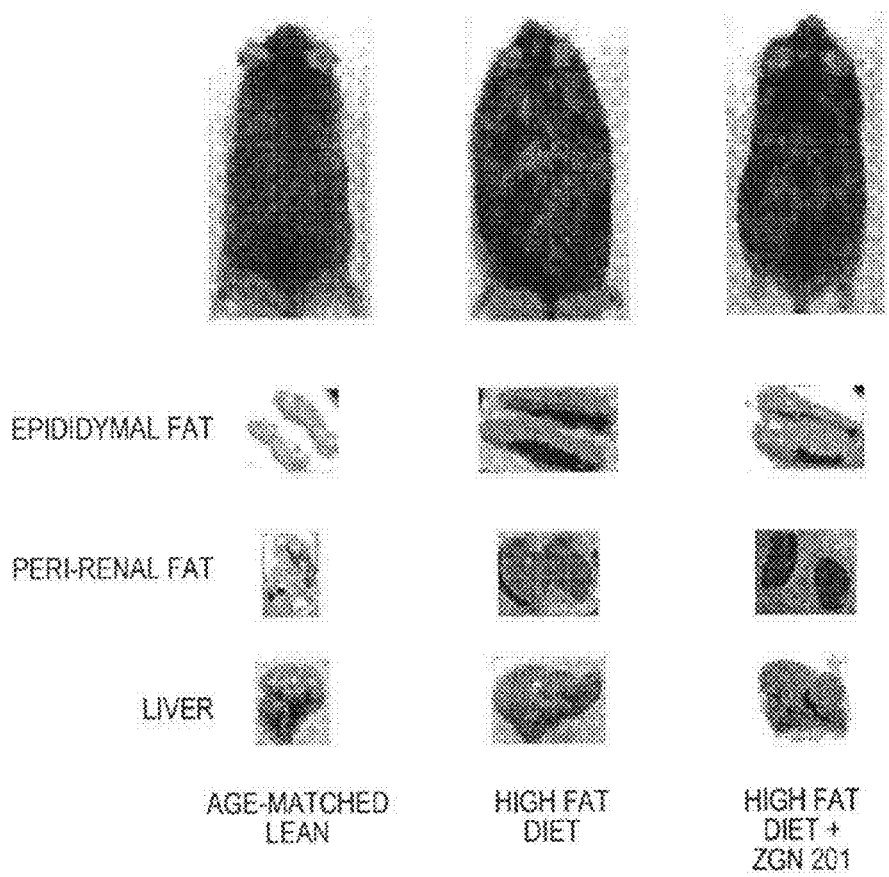
FIG. 7 shows age-matched lean mice maintained on normal mouse chow diet (left) or mice fed a high fat diet-fed and treated with 1 mg/kg fumagillin (right) or vehicle (middle) for 250 days.
Figure 8:
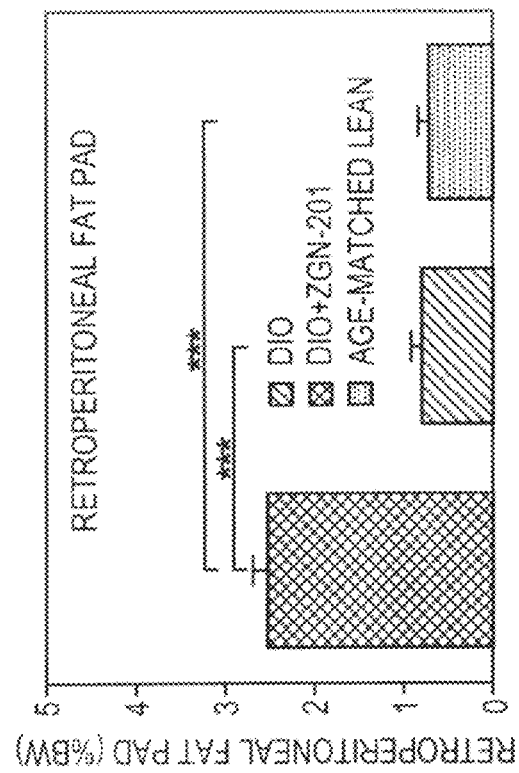
FIG. 8 contains two bar graphs showing a comparison of retroperitoneal fat pad weight in grams (left graph) and as a percentage of total body weight (right graph) for mice fed a high-fat diet (diet-induced obesity (DIO), left bar), mice fed a high-fat diet plus 1 mg/kg fumagillin (DIO+ZGN-201, middle bar), and age-matched lean mice (right bar).
Figure 8:
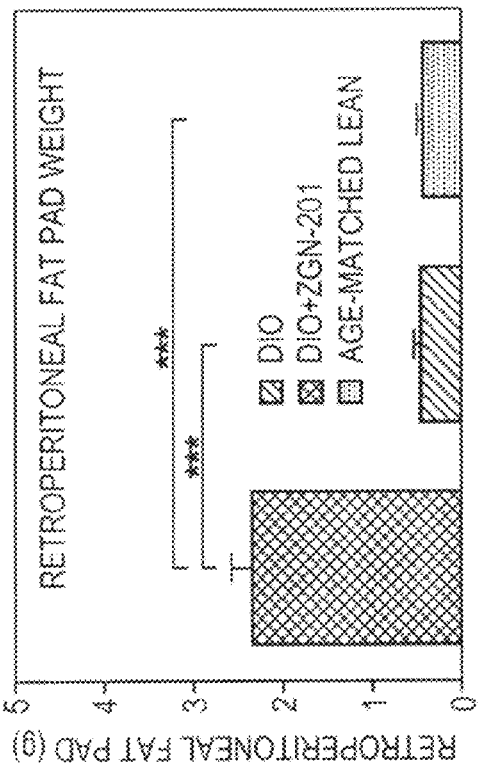

In addition to showing an increase in beta hydroxybutyrate concentration, C57BL/6 mice conditioned on a high fat diet and treated with fumagillin (ZGN-201) as a diet admixture (1 mg/kg daily for 250 days) also experienced a reduction in body fat by approximately 40 percent (FIG. 6). Once attaining the maximum weight reduction, mice treated daily with 1 mg/kg fumagillin maintained a weight that was 25% less than that of age-matched mice maintained on normal mouse chow diet (lean mice. FIG. 6) for the duration of the experiment. The size and appearance of epididymal fat, peri-renal fat and liver in fumagillin-treated mice was more similar to that of age-matched lean mice than that of untreated mice on a high fat diet (FIG. 7). Retroperitoneal fat pad weight in fumagillin-treated mice was also more similar to that of age-matched lean mice than that of untreated mice on a high fat diet (FIG. 8).

Adipose tissue in mice fed a high-fat diet show distinctive crown-like structures not seen in lean mice. These crown-like structures were also absent from the adipose tissue of fumagillin-treated mice. Additionally, adipocyte size in fumagillin-treated mice was more similar to that of age-matched lean mice than that of untreated mice on a high fat diet.

Figure 9:
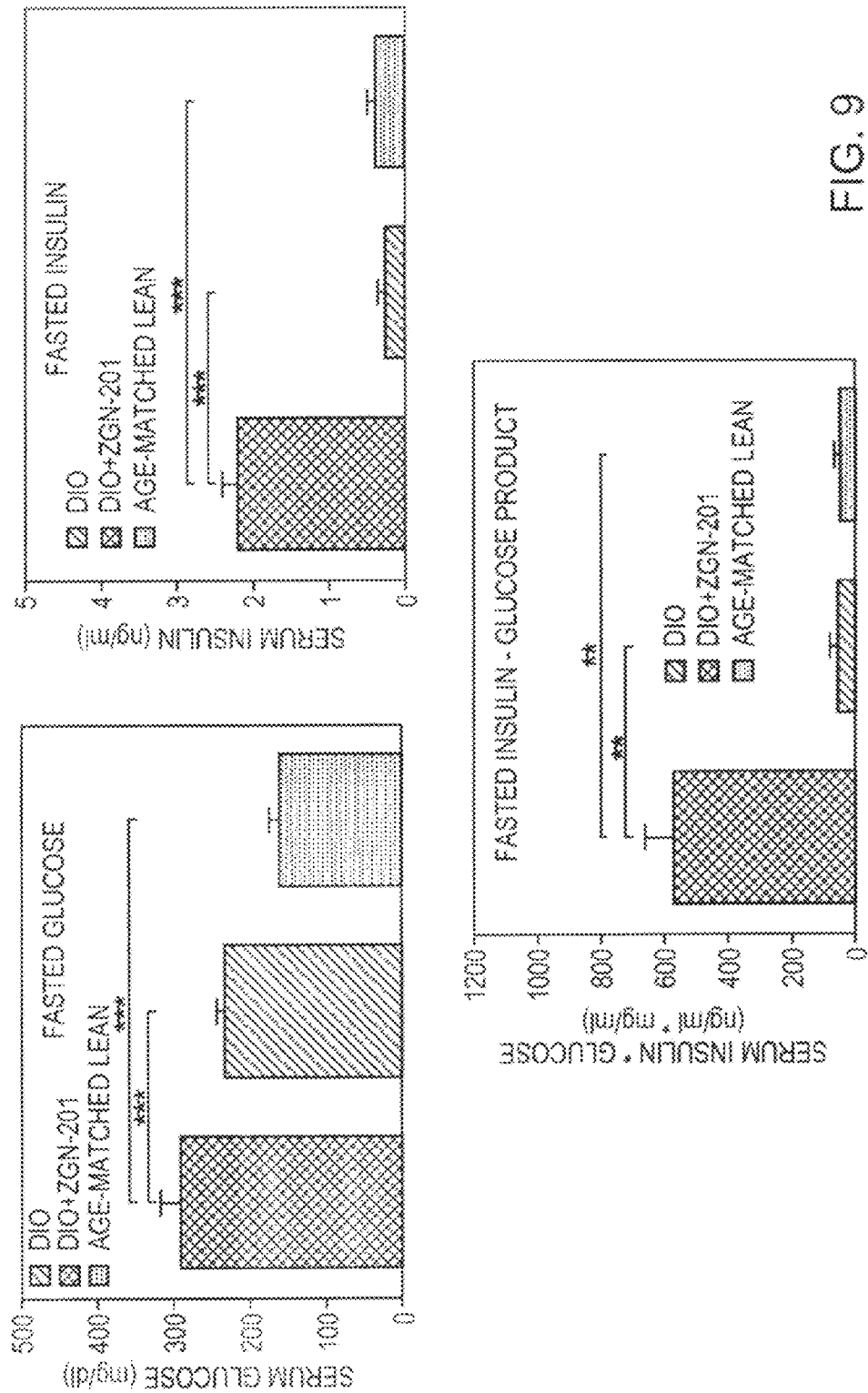
FIG. 9 contains three bar graphs showing concentrations of glucose (top left graph), insulin (top right graph) and glucose-insulin complex (bottom graph) in mice fed a high-fat diet (diet-induced obesity (DIO, left bar), mice fed a high-fat diet plus 1 mg/kg fumagillin (DIO+ZGN-201, middle bar), and age-matched lean mice (right bar).

Fasted glucose and insulin levels, as well as insulin-glucose product, in fumagillin-treated mice were more similar to that of age-matched lean mice than that of untreated mice on a high fat diet (FIG. 9), indicating that fumagillin normalizes sensitivity to insulin in mice on a high fat diet.

Example 3

Fumagillin Reduces Food Intake During the Peak of Weight Loss

Figure 10:
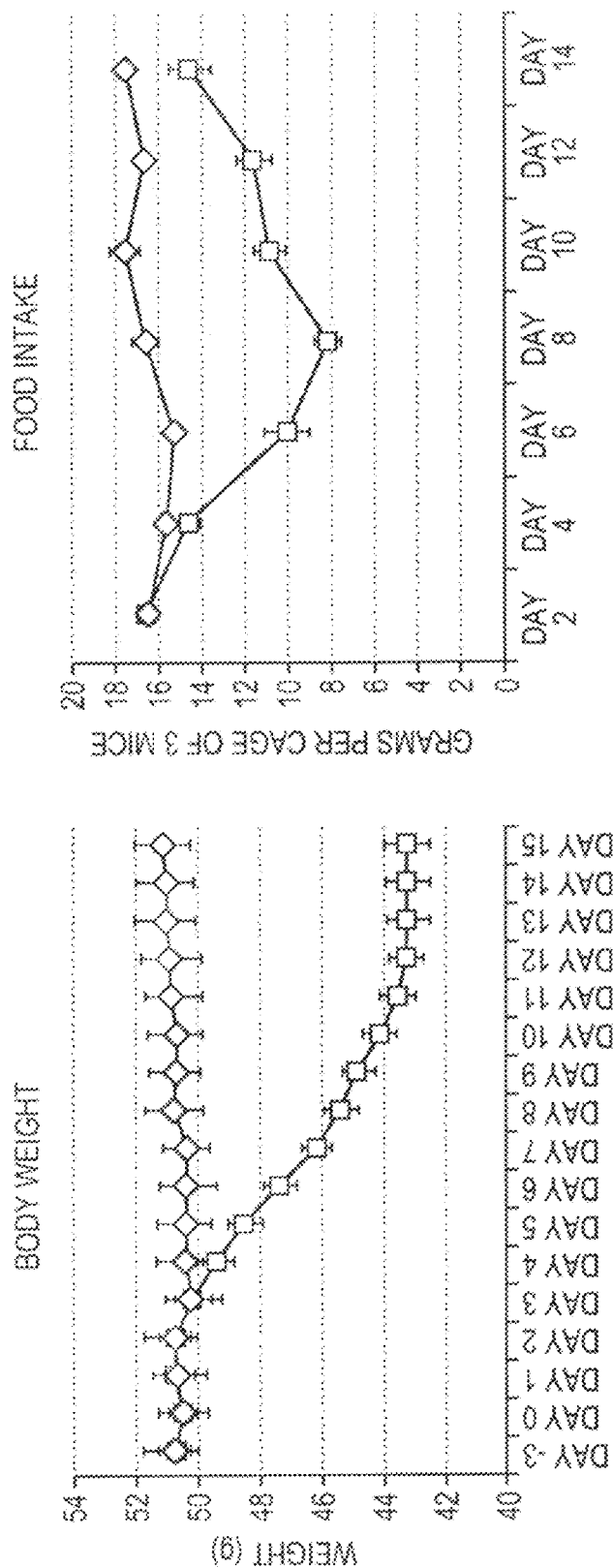
FIG. 10 shows two line graphs displaying body weight (left graph) and food intake (right graph) of mice fed a high fat diet-fed C57BL/6 mice and treated with 1 mg/kg of the MetAP2 inhibitor fumagillin (squares) or vehicle (diamonds) for 14 days.

High fat diet-fed C57BL/6 mice were treated with 1 mg/kg of the MetAP2 inhibitor fumagillin (ZGN-201, squares) or vehicle (diamonds) for 14 days (FIG. 10). Body weights (left panel) were determined daily, while food intake (right panel) was assessed every other day by measuring the food consumed by each cage of three mice over the two day period. Data shown in FIG. 10 are means±SEM, n=9 animals. As illustrated in FIG. 10, weight loss during treatment with MetAP2 inhibitors follows a sequence of three distinct phases. First, during the initial two to three days of treatment, no overt changes in food intake or body weight are observed. During this time period key changes in MetAP2 substrates occur, including glyceraldehydehyde-3-phosphate dehydrogenase and thioredoxin (data not shown). Second, the animals enter a period of rapid weight loss that proceeds until essentially all excess fat deposits are consumed. During this second period, fat oxidation is enhanced and food intake is inhibited.

Weight loss following treatment with therapeutically relevant doses of MetAP2 inhibitors stops once animals attain a normal body composition. Once weight loss reaches a nadir, fumagillin-treated animals enter a third phase in which their food intake returns to normal levels despite maintaining a normal body weight and improved metabolic control evidenced by reduced insulin and glucose concentrations. This third phase can be maintained indefinitely provided the drug is continued (see FIG. 10), or presumably can be maintained in practice through other complementary pharmacologic, dietary, or lifestyle interventions.

Example 4

Figure 11:
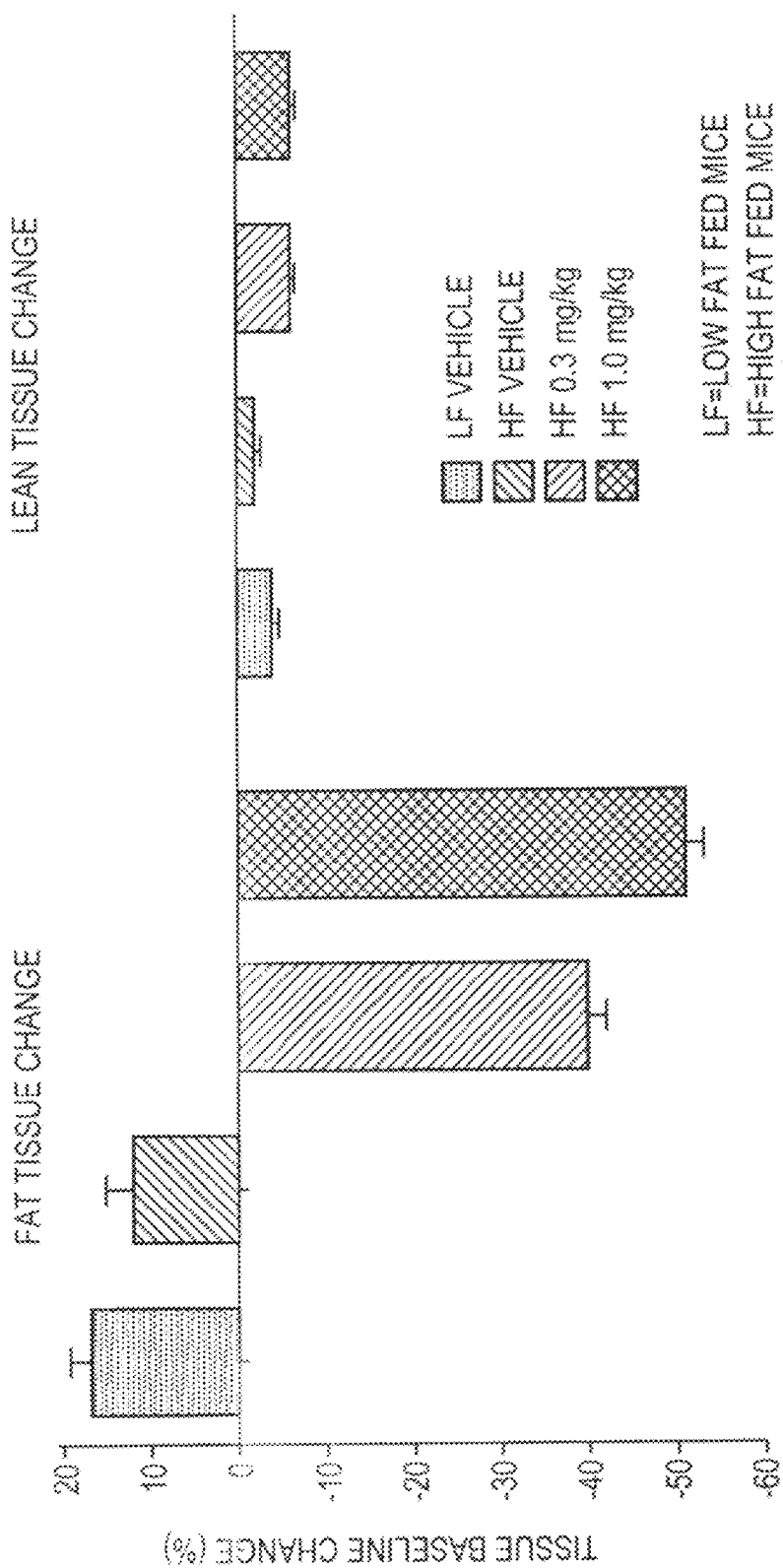
FIG. 11 is a bar graph showing the percentage change in fat tissue and lean tissue in mice conditioned on a high fat (HF) diet, mice conditioned on a high-fat diet and treated with fumagillin (ZGN-201) administered by oral gavage at doses of 0.1 or 0.3 mg/kg daily, or mice fed on a low-fat diet for 28 days. For each of "Fat Tissue Change" and "Lean Tissue Change," bars from left to right are: LF, HF, HF+0.3, and HF+0.1.
Figure 12:
FIG. 12 contains two histological images showing a comparison of retroperitoneal fat pad brown adipose tissue content for mice fed a high-fat diet (diet-induced obesity (DIO)) (left image), and mice fed a high-fat diet plus 1 mg/kg fumagillin (DIO+ZGN-201 (right image).
Figure 12:
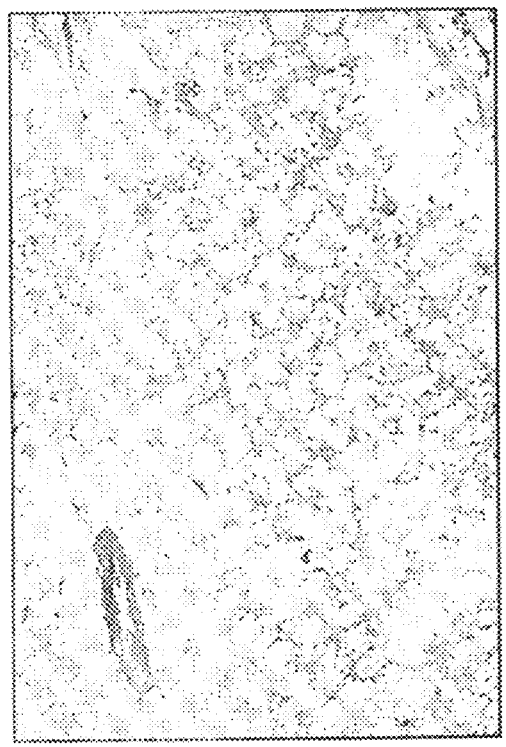

Oral Administration of Fumagillin Results in Fat Loss with Minimal Change in Lean Tissue C57BL/6 mice were conditioned on a low-fat diet (LF), a high fat diet (HF), or a high-fat diet and treated with fumagillin (ZGN-201) administered by oral gavage at doses of 0.1 or 0.3 mg/kg for 28 days. Either dose of fumagillin caused a reduction in body weight down to the level of low fat fed mice. To determine whether the weight loss resulted from loss of fat or loss of lean tissue, the percentage change in fat tissue and lean tissue was determined for LF mice. HF mice, HF mice treated with 0.1 mg/kg fumagillin, and HF mice treated with 0.3 mg/kg fumagillin. As shown in FIG. 11, HF mice treated with either dose of fumagillin experienced a 40-50% reduction in fat (compared to an increase in fat in both the LF and HF control mice), but only a 5-10% reduction in lean tissue, indicating that fumagillin-induced weight loss results primarily from loss of fat, rather than loss of lean tissue.

Upon histological examination, the studies of treated obese mice show no effect on growth of new blood vessels in growing fat depots and no effect on blood vessel size or density when compared to animals in which weight loss has been induced by simple energy (food) restriction.

Example 5

Orally Administered Compounds Having MetAP-2 Inhibitory Cores Cause Weight Loss in Diet-induced Obese Mice A weight loss study was conducted in obese mice. The mice in this study were not genetically obese, but prior to and during the study, obesity was induced by a high-fat diet. Twelve week-old C57BL/6NTac mice, maintained on a 60% fat diet prior to and during the study, were separated into seven groups, eight animals per group. Average body weight of the mice was approximately 47 g at the start of the study.

Each of six groups was orally administered 1.0 mg/kg of a compound (fumagillin and compounds B, C, D, E, F and G as disclosed herein), in 10% gelucire in deionised water. Each of these six groups was administered a different compound. One group was orally administered fumagillin at 1.0 mg/kg (group 201) in 10% gelucire in deionised water, and one group was administered 10% gelucire in deionised water (vehicle). Mice received administrations once a day for 7 days.

Figure 13:
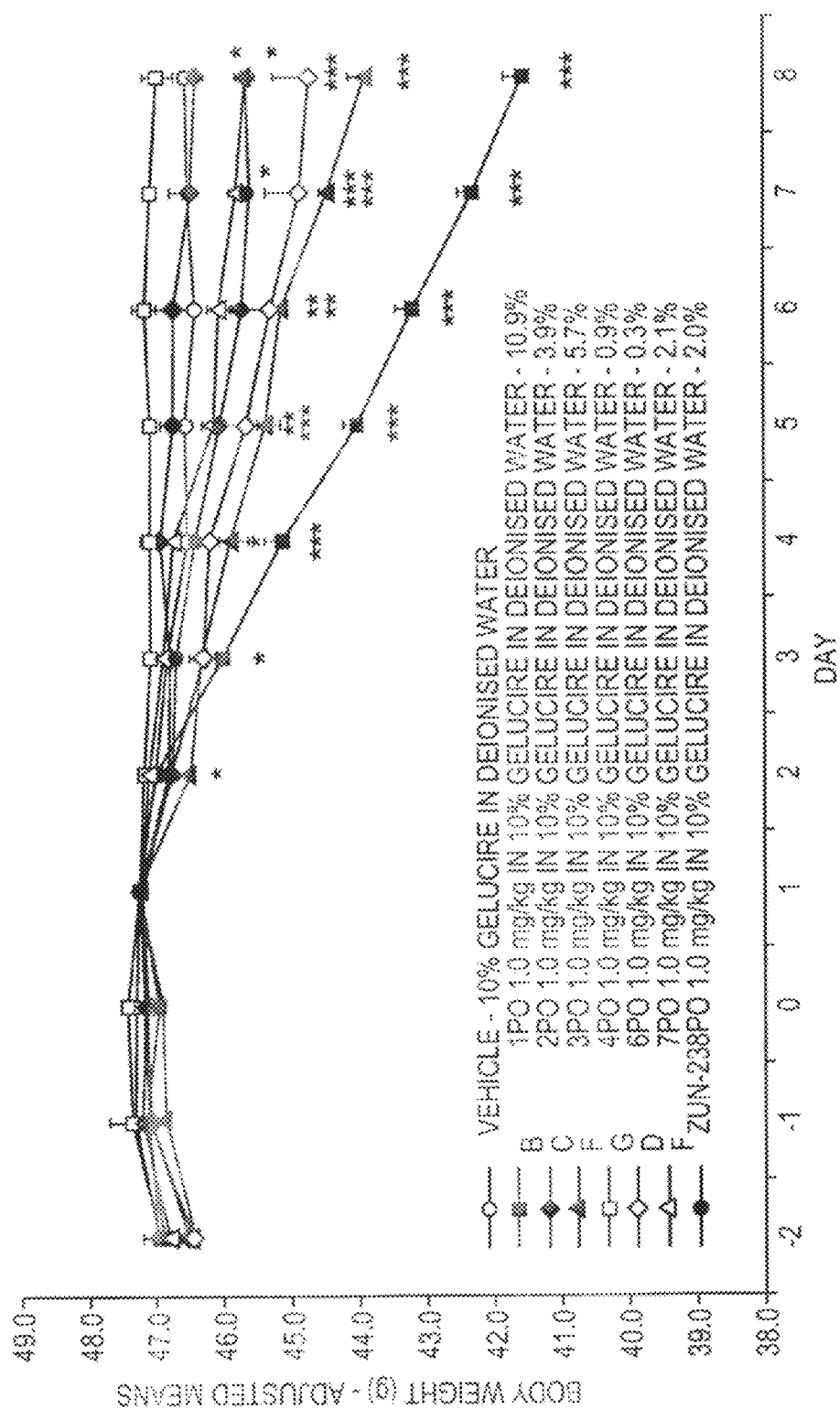
FIG. 13 depicts the effect of 7 day administration of various MetAP2 inhibitors on body weight in DIO mice.

Data show that mice administered fumagillin lost the most weight over the course of the 8 days (FIG. 13). Mice in groups B, C, E, and E also lost weight over the course of the 8 days, with mice in group 233 losing the most weight of these four groups (FIG. 13). (Data analyzed by ANCOVA with body weight on Day 1 as covariate followed by multiple tests against vehicle group: *p<0.05; p<0.01; *p<0.001.)

Example 6

A weight loss study was conducted in obese mice, similar to Example 5. Twelve week-old C57BL/6NTac mice, maintained on a 60% fat diet prior to and during the study, were separated into seven groups, eight animals per group. Average body weight of the mice was approximately 47 g at the start of the study.

The group was orally administered 100.0 mg/kg of a compound H, in 10% gelucire in deionised water. Mice received administrations once a day for 7 days. After 7 days, the average weight loss of the mice was 13.2%.

Example 7

Normalization of Glucose Tolerance in Overweight Dogs

Feeding with a high-fat high-fructose (HFF) diet in dogs has been observed to induce a selective hepatic insulin resistance, reducing liver glucose extraction and causing glucose intolerance. The effects of an 8 week treatment with ZGN-201 (ZGN) on body weight and metabolic parameters in 6 overweight dogs (3 HFF and 3 chow-fed (OWC)) were evaluated. The study was comprised of three phases—pretreatment (PT: 4 weeks), treatment (ZGNTx: 8 weeks), and washout (WO: 4 weeks). FI, BW, blood chemistry and hematology, beta-hydroxybutyrate (BHB), and glycerol were assessed weekly. Oral glucose tolerance tests (OGTT, 0.9 g/kg initial BW) were performed at the end of PT, ZGNTx, and WO.

Figure 14:
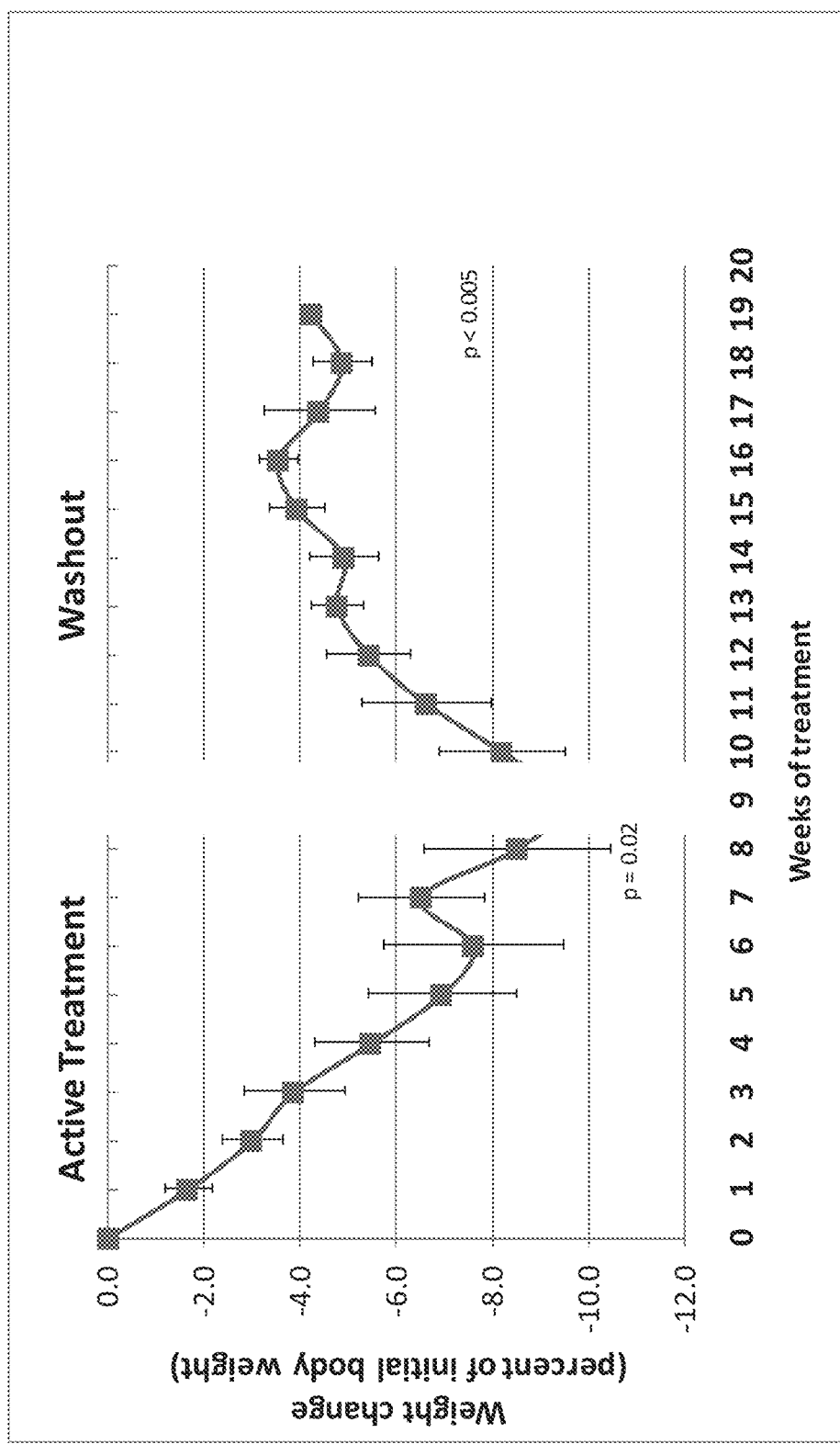
FIG. 14 depicts the effect of an 8 week treatment with fumagillin (ZGN-201) administered once daily by oral gavage on body weight in overweight dogs.

In HFF dogs, daily oral treatment with ZGN promoted loss of 81% of excess BW (resulting in a loss of approximately 8 percent of body weight, see FIG. 14), whereas treatment in OWC dogs inhibited weight gain. ZGN reduced FI in HFF dogs by 29%, but had minimal effect (9% reduction) on FI in OWC dogs. After discontinuation of treatment, weight loss in HFF dogs was sustained, where approximately one half of the initial weight loss was sustained after eight to ten weeks following the treatment discontinuation (See FIG. 14). Glycerol levels increased, reflecting enhanced lipolysis, while BHB levels, reflecting fat oxidation, were increased in HFF only.

| Endpoint | High-fat high fructose | | | Overweight chow | | |
| --- | --- | --- | --- | --- | --- | --- |
| | PT | ZGNTx | WO | PT | ZGNTx | WO |
| BW (kg) | 33.5 ± 2.6 | 30.8 ± 3.4* | 31.7 ± 2.9 | 17.7 ± 0.2 | 17.8 ± 0.5 | 18.6 ± 0.7 |
| FI (kcal/d) | 1677 ± 262 | 1187 ± 258* | 1657 ± 147 | 1365 ± 60 | 1255 ± 64* | 1116 ± 22* |
| Glycerol (μM) | 72 ± 10 | 131 ± 54* | 66 ± 25 | 94 ± 9 | 143 ± 26 | 86 ± 33 |
| BHB (μM) | 51 ± 13 | 76 ± 9* | 39 ± 7 | 41 ± 9 | 48 ± 11 | 44 ± 5 |

*p < 0.05 vs. PT

Figure 15:
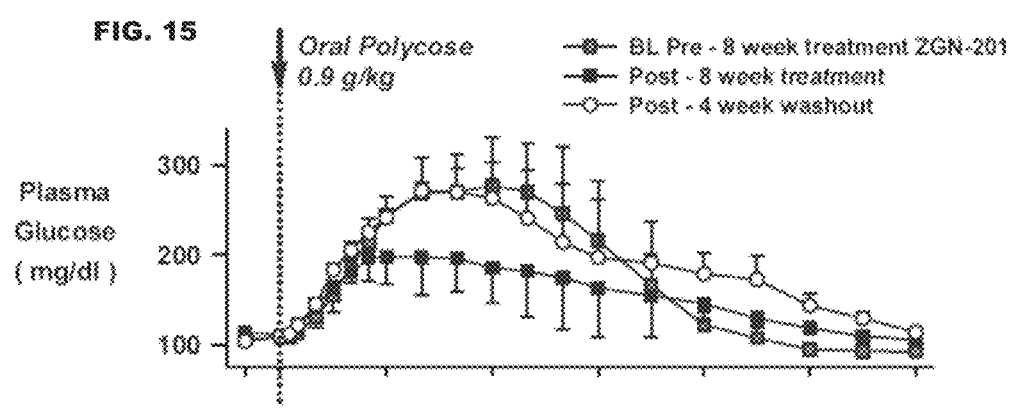
FIG. 15 depicts the effect of an 8 week treatment with fumagillin (ZGN-201) administered once daily by oral gavage on oral glucose tolerance in overweight dogs.

ZGN treatment reversed 75% of the abnormality in the plasma glucose excursion during the OGTT (see FIG. 15), despite a 32% reduction in insulin secretion (C-peptide AUC). After the drug was washed out, the improvement in plasma glucose was completely reversed. These results suggest that ZGN-201 treatment appears to correct the defect in hepatic glucose uptake seen in this model, and thereby decreases the demand for beta cell insulin secretion.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes, including PCT/US09/66816.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of inhibiting further weight gain in a patient in need thereof, wherein the patient is overweight and is not obese, comprising administering a pharmaceutically effective amount of a MetAP2 inhibitor selected from the group consisting of fumagillin, fumagillol, O-(4-dimethylaminoethoxycinnamoyl) fumagillol and pharmaceutically acceptable salts thereof to the patient; and wherein upon discontinuation of administration of said MetAP2 inhibitor, weight gain is further inhibited in the patient at least for about 1 month.

2. The method of claim 1, wherein said MetAP2 inhibitor is administered subcutaneously or intravenously.

3. The method of claim 1, wherein said MetAP2 inhibitor is selected from the group consisting of fumagillin, fumagillol and pharmaceutically acceptable salts thereof.

4. The method of claim 1, wherein said MetAP2 inhibitor is selected from O-(4-dimethylaminoethoxycinnamoyl) fumagillol and pharmaceutically acceptable salts thereof.

5. The method of claim 1, wherein administering results in decreased body fat and a substantial maintenance of muscle mass in said patient.

6. The method of claim 1, wherein upon administration, fat oxidation is enhanced as compared to a patient on a restricted food intake diet alone.

7. The method of claim 1, further comprising co-administering an additional weight loss agent.

8. The method of claim 1, further comprising administering a food restricted diet to said patient.

9. The method of claim 1, wherein said administration occurs at least daily.

10. The method of claim 1, wherein said administration occurs at least weekly.

* * * * *